(12) United States Patent
Rafalski et al.

(10) Patent No.: US 6,479,733 B1
(45) Date of Patent: Nov. 12, 2002

(54) STEROL METABOLISM ENZYMES

(75) Inventors: J. Antoni Rafalski, Wilmington; Omolayo O. Famodu, Newark, both of DE (US)

(73) Assignee: E. I. du Pont de Nemours and Company, Wilmington, DE (US)

(*) Notice: Subject to any disclaimer, the term of this patent is extended or adjusted under 35 U.S.C. 154(b) by 0 days.

(21) Appl. No.: 09/439,554

(22) Filed: Nov. 12, 1999

Related U.S. Application Data

(60) Provisional application No. 60/108,351, filed on Nov. 13, 1998.

(51) Int. Cl.[7] .................. A01H 11/00; A01H 1/00; C12N 9/00; C07H 21/04
(52) U.S. Cl. .................. 800/295; 800/278; 435/6; 435/69.1; 435/70.1; 435/183; 435/410; 435/419; 435/320.1; 530/370; 536/23.1; 536/23.2; 536/23.6; 536/24.1; 536/24.3; 536/24.33
(58) Field of Search .................. 536/23.1, 23.2, 536/23.6, 24.1, 24.3, 24.33; 435/6, 69.1, 70.1, 183, 410; 530/370; 800/278, 295

(56) References Cited

PUBLICATIONS

Bork (Genome Research Vol. 10, 2000, pp. 398–400).*
GenEmbl Accession No. AF169799.*
N_Geneseq Accession No. AAA36678.*
Russell et al. Journal of Molecular Biology, 244 (3):332–350, 1994.*
Li and Kaplan (1996) J. Biol. Chem. 271:16927–16933.
Shi et al. (1996) J. Biol. Chem. 271:9384–9389.
Bouvier —Nave et al. (1997) Eur. J. Biochem. 246:518–529.
Fujioka et al. (1997) Plant Cell 9:1951–1962.
NCBI General Identifier No. 5069775.
NCBI General Identifier No. 4966861.
NCBI General Identifier No. 4966892.
NCBI General Identifier No. 6031650.
NCBI General Identifier No. 5509139.
NCBI General Identifier No. 5753639.
NCBI General Identifier No. 4313622.
NCBI General Identifier No. 5820099.
NCBI General Identifier No. 6070142.
NCBI General Identifier No. 6070563.
NCBI General Identifier No. 2827552.
NCBI General Identifier No. 2605606.
Neuroscience 80(2):501–509 (1997).
NCBI General Indentifier No. 2498340.
NCBI General Indentifier No. 3980396.
Nature 402:761–768 (1999).
NCBI General Identifier No. 5803157.
NCBI General Identifier No. 1280611.
Science 272(5260):398–401 (1996).
NCBI General Identifier No. 2507119.
Biochim. Biophys. Acta 1305(3):139–144 (1996).
J. Biol. Chem. 264(27):16249–16255 (1989).
Li et al. (1997) PNAS 94:3554–3559.
NCBI General Identifier No. 4589974.
NCBI General Identifier No. 2246454.
NCBI General Identifier No. 2129517.
FEBS Lett. 381 (1–2):87–92 (1996).
NCBI General Identifier No. 3560533.
Eur. J. Biochem. 256(1):88–96 (1998).
Schaller et al. (1998) Plant Phys. 118:461–469.
Houston et al. (1985) J. Steroid Biochem. 22:461–467.

* cited by examiner

*Primary Examiner*—Phuong T. Bui
*Assistant Examiner*—Alexander H. Spiegler

(57) ABSTRACT

This invention relates to an isolated nucleic acid fragment encoding a sterol metabolism enzyme. The invention also relates to the construction of a chimeric gene encoding all or a portion of the sterol metabolism enzyme, in sense or antisense orientation, wherein expression of the chimeric gene results in production of altered levels of the sterol metabolism enzyme in a transformed host cell.

12 Claims, No Drawings

SEQUENCE LISTING

<160> NUMBER OF SEQ ID NOS: 30

<210> SEQ ID NO 1
<211> LENGTH: 497
<212> TYPE: DNA
<213> ORGANISM: Zea mays

<400> SEQUENCE: 1

```
ccaggctcag cctcccctct cccctcctcg gcatcttcgc cgccgggatc tatctctctc     60
acaatggcgg cgcccatgtc agccatcgac tcagcgtggc agctcctgat cgccaacttc    120
accgagttcc agctcgccac cgtcgtcacc ttcctgctcc acgagaccgt cttcttcctc    180
tccggcctcc cctccctcct cttcgagcgc ttcggactct tcgccaagta caagatccag    240
aagaagagca cacctctgc ttaccaaaac agatgtgtct tgcgcctcat tctctaccat    300
gtatgtgtga acctgcctgt catgattttc tcgtatcctg ccttcaaatt catgggtctc    360
aggagctctc ttcctttgcc acattggtcg gttgttgtat ctcaagttct tttctacttt    420
gtccttgagg attttatatt ctattggggg caagggcatt gcatacgaaa tggctataca    480
aacacgttca cagcgtc                                                   497
```

<210> SEQ ID NO 2
<211> LENGTH: 81
<212> TYPE: PRT
<213> ORGANISM: Zea mays

<400> SEQUENCE: 2

```
Ser Ala Trp Gln Leu Leu Ile Ala Asn Phe Thr Glu Phe Gln Leu Ala
 1               5                  10                  15

Thr Val Val Thr Phe Leu Leu His Glu Thr Val Phe Phe Leu Ser Gly
                20                  25                  30

Leu Pro Ser Leu Leu Phe Glu Arg Phe Gly Leu Phe Ala Lys Tyr Lys
                35                  40                  45

Ile Gln Lys Ser Asn Thr Ser Ala Tyr Gln Asn Arg Cys Val Leu Arg
 50                  55                  60

Leu Ile Leu Tyr His Val Cys Val Asn Leu Pro Val Met Ile Phe Ser
 65                  70                  75                  80

Tyr
```

<210> SEQ ID NO 3
<211> LENGTH: 593
<212> TYPE: DNA
<213> ORGANISM: Oryza sativa
<220> FEATURE:
<221> NAME/KEY: unsure
<222> LOCATION: (383)
<220> FEATURE:
<221> NAME/KEY: unsure
<222> LOCATION: (412)
<220> FEATURE:
<221> NAME/KEY: unsure
<222> LOCATION: (548)
<220> FEATURE:
<221> NAME/KEY: unsure
<222> LOCATION: (570)

<400> SEQUENCE: 3

```
caattgttgg tccggccctc actggtccgc acttgttcac tctatggctg tggatggtgt     60
tgagggtatt ggagacagtt gaagctcaca gtggatacca tttcccatgg agcccatcaa   120
```

-continued

```
atttcttgcc actgtatgga ggctccgact ttcatgacta tcatcaccgt gtgctctaca      180
ccaaatcagg aaactacgcc tctacttttg tttacatgga ctggctgttt ggcacggaca      240
aggattaccg caatgccaag gctatcgagg agaaagacgg gaagcatttg taaattgtgg      300
gggctacctc tttctctttg tccaaatcat cgaaacaagg gtttgacatc tcgcaatggg      360
tgatacattg tgttcaatgg gangaaatag tgtcctagcc acaggtatct anctcctgag      420
atgatcctac atttaatttc cttccccaaa ttcactatac tacatcatga gacttgggtt      480
ctggaggcac atgattattt gcataaacta attgagcgtg cattgtggtt gctggacggg      540
gacatcanac agaatgaaca tcaacagaan tgcagatatg agtactaaaa aaa            593
```

<210> SEQ ID NO 4
<211> LENGTH: 54
<212> TYPE: PRT
<213> ORGANISM: Oryza sativa

<400> SEQUENCE: 4

Val Gly Pro Ala Leu Thr Gly Pro His Leu Phe Thr Leu Trp Leu Trp
1               5                   10                  15

Met Val Leu Arg Val Leu Glu Thr Val Glu Ala His Ser Gly Tyr His
                20                  25                  30

Phe Pro Trp Ser Pro Ser Asn Phe Leu Pro Leu Tyr Gly Gly Ser Asp
        35                  40                  45

Phe His Asp Tyr His His
        50

<210> SEQ ID NO 5
<211> LENGTH: 614
<212> TYPE: DNA
<213> ORGANISM: Glycine max
<220> FEATURE:
<221> NAME/KEY: unsure
<222> LOCATION: (502)
<220> FEATURE:
<221> NAME/KEY: unsure
<222> LOCATION: (582)..(583)
<220> FEATURE:
<221> NAME/KEY: unsure
<222> LOCATION: (596)
<220> FEATURE:
<221> NAME/KEY: unsure
<222> LOCATION: (602)
<220> FEATURE:
<221> NAME/KEY: unsure
<222> LOCATION: (606)
<220> FEATURE:
<221> NAME/KEY: unsure
<222> LOCATION: (610)

<400> SEQUENCE: 5

```
gcatccactt ccccactctc tcacatattg cctctctctt tcctctttcc attgtccatg       60
gcgtccctca tcgaatctgg ctggcagtac ttgatcacac atttcagtga ctttcaactg      120
gcgtgtttgg gaagtttctt tctacatgaa ggcgttttct tcttgtctgg acttcccttt      180
atatggcttg agagggcagg gtggatgagc aagtacaaaa ttcaggccaa aaataacacc      240
cctgcagctc aggagaaatg tattgttcgt ctgttgcttt accatttttgg gtgtcaatct      300 acctgttatg attttttcat atcctgtctt cacatacatg ggcatgcgga gtaagtcttc      360
ccctaccgtc ctgggaaagt agtccaattc aaataacttt tacttcattt tgggaggact      420
ttatattcct actgggggac atagaatact gcacacaaag tggttataca agcatgtgca      480
caagtgttca acaagaagta tngctacacc gtttgggatt acttcggaat atccatcctg      540
```

```
ctgaatattt ccctgggggtt gctacatttt ggcctgcatt annggggccca cttganatcc      600 cnggtnaggn ggtc                                                         614
```

<210> SEQ ID NO 6
<211> LENGTH: 74
<212> TYPE: PRT
<213> ORGANISM: Glycine max

<400> SEQUENCE: 6

```
Glu Ser Gly Trp Gln Tyr Leu Ile Thr His Phe Ser Asp Phe Gln Leu
 1               5                  10                  15

Ala Cys Leu Gly Ser Phe Phe Leu His Glu Gly Val Phe Phe Leu Ser
            20                  25                  30

Gly Leu Pro Phe Ile Trp Leu Glu Arg Ala Gly Trp Met Ser Lys Tyr
        35                  40                  45

Lys Ile Gln Ala Lys Asn Asn Thr Pro Ala Ala Gln Glu Lys Cys Ile
    50                  55                  60

Val Arg Leu Leu Leu Tyr His Phe Gly Cys
 65                  70
```

<210> SEQ ID NO 7
<211> LENGTH: 776
<212> TYPE: DNA
<213> ORGANISM: Triticum aestivum
<220> FEATURE:
<221> NAME/KEY: unsure
<222> LOCATION: (573)
<220> FEATURE:
<221> NAME/KEY: unsure
<222> LOCATION: (653)
<220> FEATURE:
<221> NAME/KEY: unsure
<222> LOCATION: (667)
<220> FEATURE:
<221> NAME/KEY: unsure
<222> LOCATION: (682)
<220> FEATURE:
<221> NAME/KEY: unsure
<222> LOCATION: (743)

<400> SEQUENCE: 7

```
atctcaagtt cttttttatt ttatactcga agatttcata ttctattggg ggcacagggc       60
tctgcatacc aaatggctat acaagcatgt ccacagtgtg caccatgaat atgctacacc      120
attcggctta acttcggaat atgcacaccc tgctgaaatt ttgttcctgg gatttgccac      180
ggttgttggt cctgccctga ccggccctca cttgttcacc ctttggctgt ggatggtttt      240
gagggtgtta gagacggttg aagctcacag tggatatcac ttcccttgga gcccatcaaa      300
cttcctgcca ctgtatggag gctctgactt ccatgactac catcatcgtg tgctgtacac      360
caagtcagga aactacgcct ctactttgt ttacatggac tggttgtttg gcacagataa      420
gggttatcgc aagacaaaag ccatcgaagg ggaagaaggg aagcattttg taaattgtgg      480
gaggctactc tctcttttct cctgaagtca actcatcaag aactaatttt tggatctcct      540
tgtattgggt gataacattg tgttcatggg ganggagata cacgcggcat cgattcctag      600
gcatgggccg tcgctcctac atgtccgttg atctctgttc tcccatattt gcnaagcatg      660
atgaagncaa tgtgttgtgt anggcaactt atataatttg ggggtgaatt aaatatgttg      720
tgctctgttg gggtttgttt ggncatatgc ccatgacaag ctaattctc catatt          776
```

<210> SEQ ID NO 8

```
<211> LENGTH: 108
<212> TYPE: PRT
<213> ORGANISM: Triticum aestivum

<400> SEQUENCE: 8

Ile Leu Glu Asp Phe Ile Phe Tyr Trp Gly His Arg Ala Leu His Thr
 1               5                  10                  15

Lys Trp Leu Tyr Lys His Val His Ser Val His Glu Tyr Ala Thr
            20                  25                  30

Pro Phe Gly Leu Thr Ser Glu Tyr Ala His Pro Ala Glu Ile Leu Phe
        35                  40                  45

Leu Gly Phe Ala Thr Val Val Gly Pro Ala Leu Thr Gly Pro His Leu
    50                  55                  60

Phe Thr Leu Trp Leu Trp Met Val Leu Arg Val Leu Glu Thr Val Glu
65                  70                  75                  80

Ala His Ser Gly Tyr His Phe Pro Trp Ser Pro Ser Asn Phe Leu Pro
                85                  90                  95

Leu Tyr Gly Gly Ser Asp Phe His Asp Tyr His His
            100                 105

<210> SEQ ID NO 9
<211> LENGTH: 468
<212> TYPE: DNA
<213> ORGANISM: Zea mays
<220> FEATURE:
<221> NAME/KEY: unsure
<222> LOCATION: (456)

<400> SEQUENCE: 9
ggggcgggtg gttcgacctc gtcaccagcc ccaattactt cggcgagacg gtggagtggc      60
tgggcttcgc cgtggtggcg tggacgcccg cggcctgggc gttcttcctc tacacctgcg     120
ccaacctcgg gccgagggcc aggaccacc gccgctggta cgtgcagaag ttccgcggcg      180
agtacccggc gtcgcgcaag gcgttcatcc cctacatcta ctaggtgatg ccgtggtttt     240
cggttcgttc ttcttggccg ccttatcttc cttcgcggcg gagcagaagc aggagagcag     300
gctgagtttg cccatgtttc gactcgacga gaaggcgagt agacacagag aacctgcgat     360
gcgattagct gcgcgagact gcaacctgtt gaatctaatg ttctacattg ctgctgtcat     420
gattatagat gtacaggcag attaatataa gcggcnagga taactgtt                  468

<210> SEQ ID NO 10
<211> LENGTH: 73
<212> TYPE: PRT
<213> ORGANISM: Zea mays

<400> SEQUENCE: 10

Gly Gly Trp Phe Asp Leu Val Thr Ser Pro Asn Tyr Phe Gly Glu Thr
 1               5                  10                  15

Val Glu Trp Leu Gly Phe Ala Val Val Ala Trp Thr Pro Ala Ala Trp
            20                  25                  30

Ala Phe Phe Leu Tyr Thr Cys Ala Asn Leu Gly Pro Arg Ala Arg Asp
        35                  40                  45

His Arg Arg Trp Tyr Val Gln Lys Phe Arg Gly Glu Tyr Pro Ala Ser
    50                  55                  60

Arg Lys Ala Phe Ile Pro Tyr Ile Tyr
65                  70

<210> SEQ ID NO 11
```

<211> LENGTH: 569
<212> TYPE: DNA
<213> ORGANISM: Triticum aestivum

<400> SEQUENCE: 11

```
gccagaccta gtcattgatt caccctctct cctaaagcct cttttaaagt tggggtggtg      60
ccagtggata ggtgctattg tattcatttg gggatccctc catcagatcc gttgtcatgc     120
aattcttgga tcgttgcgcg aaaataaaga ttctgatgaa tatgttattc cttgcggtga     180
ctggtttagt cgtgtgtctt gccctcatta ccttgctgaa ctagttatat atttgggcat     240
gttgatagct agtggtggat cagacatttc agtgtggttc ctgttcattt ttgtgataac     300
aaacttgtca tttgcagcag tacaaactca taggtggtac ctccaaaagt ttgaagacta     360
cccccgctct cgctatgcta tcattccatt tgtattgtag catctacaag cattccttct     420
gtgcagtaaa aactgtgtgt tccgggctaa gaatgcacaa gcccggcatg taaaagatat     480
catgtaaatg tgacagcatg taagttaaaa tgttgtgttg tgtgacttga aatacttaca     540
agggttcatt tcaagttgta aattgcgat                                       569
```

<210> SEQ ID NO 12
<211> LENGTH: 77
<212> TYPE: PRT
<213> ORGANISM: Triticum aestivum

<400> SEQUENCE: 12

```
Tyr Val Ile Pro Cys Gly Asp Trp Phe Ser Arg Val Ser Cys Pro His
 1               5                  10                  15

Tyr Leu Ala Glu Leu Val Ile Tyr Leu Gly Met Leu Ile Ala Ser Gly
             20                  25                  30

Gly Ser Asp Ile Ser Val Trp Phe Ile Phe Val Ile Thr Asn Leu Ser
         35                  40                  45

Phe Ala Ala Val Gln Thr His Arg Trp Tyr Leu Gln Lys Phe Glu Asp
     50                  55                  60

Tyr Pro Arg Ser Arg Tyr Ala Ile Ile Pro Phe Val Leu
 65                  70                  75
```

<210> SEQ ID NO 13
<211> LENGTH: 507
<212> TYPE: DNA
<213> ORGANISM: Zea mays
<220> FEATURE:
<221> NAME/KEY: unsure
<222> LOCATION: (459)
<220> FEATURE:
<221> NAME/KEY: unsure
<222> LOCATION: (477)

<400> SEQUENCE: 13

```
catcgccgcg cactcgggat ccaacgtcgt cggcatcacc atcaacgagt accaggtgaa      60
ccgcgcccgc gcgcaacaac cgcaaggccg gcctcgactc cccgcgctgc gaggtcgtct     120
gcggcaactt cctctccatg ccgttcccgg acgcctcctt cgacgcgcc tactccatcg     180
aggccacctg ccacgcgccc aggctgcagg acgtgtacgg cgaggtctac cgcgtgctca     240
agccgggggg actctacgtc tcctacgagt gggtcaccac cccgctgtac cgcgccgagg     300
acccggacca cgtcgagtgc atccacggca tcgagcgcgg cgacgtcccc ggggctccgc     360
gccaagaacg agatcgcgtc catcgcaaag aggtcggctt tcaagtgctc aaggagcagg     420
aactttcgtg cccccgcgct gcctggtgaa gcgctcaana tggggcgatt gctaatnggg     480
```

```
aaatccttgt gtcggtgtta catgttc                                              507
```

<210> SEQ ID NO 14
<211> LENGTH: 123
<212> TYPE: PRT
<213> ORGANISM: Zea mays

<400> SEQUENCE: 14

```
Ile Ala Ala His Ser Gly Ser Asn Val Val Gly Ile Thr Ile Asn Glu
 1               5                  10                  15

Tyr Gln Val Asn Arg Ala Arg Asn Asn Arg Lys Ala Gly Leu Asp Ser
            20                  25                  30

Pro Arg Cys Glu Val Val Cys Gly Asn Phe Leu Ser Met Pro Phe Pro
        35                  40                  45

Asp Ala Ser Phe Asp Gly Ala Tyr Ser Ile Glu Ala Thr Cys His Ala
    50                  55                  60

Pro Arg Leu Gln Asp Val Tyr Gly Glu Val Tyr Arg Val Leu Lys Pro
65                  70                  75                  80

Gly Gly Leu Tyr Val Ser Tyr Glu Trp Val Thr Thr Pro Leu Tyr Arg
                85                  90                  95

Ala Glu Asp Pro Asp His Val Glu Cys Ile His Gly Ile Glu Arg Gly
            100                 105                 110

Asp Val Pro Gly Ala Pro Arg Gln Glu Arg Asp
        115                 120
```

<210> SEQ ID NO 15
<211> LENGTH: 597
<212> TYPE: DNA
<213> ORGANISM: Oryza sativa
<220> FEATURE:
<221> NAME/KEY: unsure
<222> LOCATION: (398)
<220> FEATURE:
<221> NAME/KEY: unsure
<222> LOCATION: (407)
<220> FEATURE:
<221> NAME/KEY: unsure
<222> LOCATION: (458)..(459)
<220> FEATURE:
<221> NAME/KEY: unsure
<222> LOCATION: (503)
<220> FEATURE:
<221> NAME/KEY: unsure
<222> LOCATION: (506)
<220> FEATURE:
<221> NAME/KEY: unsure
<222> LOCATION: (528)
<220> FEATURE:
<221> NAME/KEY: unsure
<222> LOCATION: (537)
<220> FEATURE:
<221> NAME/KEY: unsure
<222> LOCATION: (578)
<220> FEATURE:
<221> NAME/KEY: unsure
<222> LOCATION: (589)
<220> FEATURE:
<221> NAME/KEY: unsure
<222> LOCATION: (596)

<400> SEQUENCE: 15

```
cgggtctccg ccgccaggac gagatcgcgt ccatcgccaa ggaggtcgga ttcgaggtgc    60
tcaaggagct cgacctcgcc ctcccgcccg ctctcccatg gtggactcgc ctcaagatgg   120
ggcgcatcgc atactggcgc aactccctcg tcgtccgcgt gctcaccatg ctccggattg   180
cacccaaggg cgtctgcgag gtgcacgaga tgctctacga gaccgcgcag cacctcaccc   240
```

```
gcggcggcga gaccggcatc ttcacgccga tgcacatggt gctcctccgc aagcccgtcg    300
aagagcaaat agtgcaacaa atcatccgac gacaacaaca acacctacct tcattcactc    360
accaagcggg aagaaacaga gggaaaacaa caaaaaanct cgcaagntta gcagtgaggt    420
aagaagacag atacctacct gggtgaagag gagagttnna agaagagatg ccttaaatta    480
attaatttga tcgtttaaag ganaanaagg tgatttatgt acctttcntg tccgtancaa    540
tttgcttcaa ttttttgggg gaggatttgg ttgaaaanaa gtcggatcnc tttaant       597
```

<210> SEQ ID NO 16
<211> LENGTH: 98
<212> TYPE: PRT
<213> ORGANISM: Oryza sativa

<400> SEQUENCE: 16

Gly Leu Arg Arg Gln Asp Glu Ile Ala Ser Ile Ala Lys Glu Val Gly
 1               5                  10                  15

Phe Glu Val Leu Lys Glu Leu Asp Leu Ala Leu Pro Pro Ala Leu Pro
                20                  25                  30

Trp Trp Thr Arg Leu Lys Met Gly Arg Ile Ala Tyr Trp Arg Asn Ser
            35                  40                  45

Leu Val Val Arg Val Leu Thr Met Leu Arg Ile Ala Pro Lys Gly Val
        50                  55                  60

Cys Glu Val His Glu Met Leu Tyr Glu Thr Ala Gln His Leu Thr Arg
 65                  70                  75                  80

Gly Gly Glu Thr Gly Ile Phe Thr Pro Met His Met Val Leu Leu Arg
                85                  90                  95

Lys Pro

<210> SEQ ID NO 17
<211> LENGTH: 637
<212> TYPE: DNA
<213> ORGANISM: Glycine max
<220> FEATURE:
<221> NAME/KEY: unsure
<222> LOCATION: (36)
<220> FEATURE:
<221> NAME/KEY: unsure
<222> LOCATION: (530)
<220> FEATURE:
<221> NAME/KEY: unsure
<222> LOCATION: (577)
<220> FEATURE:
<221> NAME/KEY: unsure
<222> LOCATION: (612)
<220> FEATURE:
<221> NAME/KEY: unsure
<222> LOCATION: (634)

<400> SEQUENCE: 17

```
gtaaaacctc acaatcacaa acacactctt ttttgntctt tgctcacttc ccttgttcgt     60
ttcactctca caatggactc cctctctctc ttctgcaccg gagcccttct cgggggcggc    120
ctctactggt tcgtctgtgt tctgggcccc gccgagcaga agggcaaacg cgccaccgat    180
ctatccggcg gctccatctc cgccgagaaa gtccaagaca actacaagca gtactggtcc    240
ttcttccgcc gccccaagga gatcgagacc gccgacaaag ttcccgactt cgtcgacacc    300
ttctacaatc tagtcaccga catctacgag tggggctggg gccagtcctt ccacttctcc    360
ccctccatcc ccggtaagtc ccaccgcgag gccacgcgcc tccacgagga gatgccgtc    420 gatctcatcg aggccaagcc cggcaacaaa atcctggacg tgggctgcgg cgtgggcggg    480
```

```
cccatgcggg ccatcgcggc ccactcccgc gcgaacgtgg tgggcatcan catcaacgaa      540
gtacaagtca atcgagcaag gatgcacaac aagaagntgg gttggctctc tctgcaagtc      600
ctgtgtggga anttcctaag atgcgtttgt cganaca                               637
```

<210> SEQ ID NO 18
<211> LENGTH: 170
<212> TYPE: PRT
<213> ORGANISM: Glycine max
<220> FEATURE:
<221> NAME/KEY: UNSURE
<222> LOCATION: (153)
<220> FEATURE:
<221> NAME/KEY: UNSURE
<222> LOCATION: (169)

<400> SEQUENCE: 18

```
Met Asp Ser Leu Ser Leu Phe Cys Thr Gly Ala Leu Leu Gly Gly
  1               5                  10                  15

Leu Tyr Trp Phe Val Cys Val Leu Gly Pro Ala Glu Gln Lys Gly Lys
                 20                  25                  30

Arg Ala Thr Asp Leu Ser Gly Gly Ser Ile Ser Ala Glu Lys Val Gln
             35                  40                  45

Asp Asn Tyr Lys Gln Tyr Trp Ser Phe Phe Arg Arg Pro Lys Glu Ile
 50                  55                  60

Glu Thr Ala Asp Lys Val Pro Asp Phe Val Asp Thr Phe Tyr Asn Leu
 65                  70                  75                  80

Val Thr Asp Ile Tyr Glu Trp Gly Trp Gly Gln Ser Phe His Phe Ser
                 85                  90                  95

Pro Ser Ile Pro Gly Lys Ser His Arg Glu Ala Thr Arg Leu His Glu
                100                 105                 110

Glu Met Ala Val Asp Leu Ile Glu Ala Lys Pro Gly Asn Lys Ile Leu
             115                 120                 125

Asp Val Gly Cys Gly Val Gly Gly Pro Met Arg Ala Ile Ala Ala His
130                 135                 140

Ser Arg Ala Asn Val Val Gly Ile Xaa Ile Asn Glu Val Gln Val Asn
145                 150                 155                 160

Arg Ala Arg Met His Asn Lys Lys Xaa Gly
                165                 170
```

<210> SEQ ID NO 19
<211> LENGTH: 1118
<212> TYPE: DNA
<213> ORGANISM: Zea mays

<400> SEQUENCE: 19

```
gcacgagcca ggctcagcct cccctctccc ctcctcggca tcttcgccgc cggcgatcta       60
tctctctcac aatggcggcg cccatgtcag ccatcgactc agcgtggcag ctcctgatcg      120
ccaacttcac cgagttccag ctcgccaccg tcgtcacctt cctgctccac gagaccgtct      180
tcttcctctc cggcctcccc tccctcctct tcgagcgctt cggactcttc gccaagtaca      240
agatccagaa gaagagcaac acctctgctt accaaaacag atgtgtcttg cgcctcattc      300
tctaccatgt atgtgtgaac ctgcctgtca tgattttctc gtatcctgcc ttcaaattca      360
tgggtctcag gagctctctt cctttgccac attggtcggt tgttgtatct caagttcttt      420
tctactttgt ccttgaggat tttatattct attggggca cagggcattg catacgaaat      480
ggctatacaa acacgttcac agcgtccacc atgagtacgc cacacccttt ggtttaacat      540
```

-continued

```
cggaatatgc ccacccagct gaaattttgt tcctgggatt cgccacagtt gttggtcctg      600
ctcttactgg ccctcatctc ttcaccctgt ggctgtggat ggtgttgagg gttttggaga      660
cagttgaagc tcacagcggc tatcacttcc catggagccc atcaaatttc ctgccgctgt      720
atggcggctc ggacttccat gactaccatc accgtgtgct gtacacaaag tcaggaact       780 atgcctcaac atttgtttac atggactggt tgttcggcac ggacaaggat tatcgcaagg      840
caaagaccat tgaggagaaa gaagggaaaa atctgtagat tgtggaagct gctcagcaag      900
actggcgata gagtttcact catggaagga gatatggatg caccctagaa acagtcagtt      960
tatctcctga ccatcgatac tataggttga gatattgatt cctgtgtttt gctatgatca     1020
agaatgaggc cctggtggcc ctggtctgtc atgaactgaa tttgatgatt tgtcatctcc     1080
tcctggtggt taaaaaaaaa aaaaaaaaaa aaaaaaaa                              1118
```

<210> SEQ ID NO 20
<211> LENGTH: 291
<212> TYPE: PRT
<213> ORGANISM: Zea mays

<400> SEQUENCE: 20

```
Thr Ser Gln Ala Gln Pro Leu Ser Pro Pro Arg His Leu Arg Arg
 1               5                  10                  15

Arg Arg Ser Ile Ser Leu Thr Met Ala Ala Pro Met Ser Ala Ile Asp
                20                  25                  30

Ser Ala Trp Gln Leu Leu Ile Ala Asn Phe Thr Glu Phe Gln Leu Ala
            35                  40                  45

Thr Val Val Thr Phe Leu Leu His Glu Thr Val Phe Phe Leu Ser Gly
        50                  55                  60

Leu Pro Ser Leu Leu Phe Glu Arg Phe Gly Leu Phe Ala Lys Tyr Lys
    65                  70                  75                  80

Ile Gln Lys Lys Ser Asn Thr Ser Ala Tyr Gln Asn Arg Cys Val Leu
                85                  90                  95

Arg Leu Ile Leu Tyr His Val Cys Val Asn Leu Pro Val Met Ile Phe
            100                 105                 110

Ser Tyr Pro Ala Phe Lys Phe Met Gly Leu Arg Ser Ser Leu Pro Leu
        115                 120                 125

Pro His Trp Ser Val Val Ser Gln Val Leu Phe Tyr Phe Val Leu
    130                 135                 140

Glu Asp Phe Ile Phe Tyr Trp Gly His Arg Ala Leu His Thr Lys Trp
145                 150                 155                 160

Leu Tyr Lys His Val His Ser Val His Glu Tyr Ala Thr Pro Phe
                165                 170                 175

Gly Leu Thr Ser Glu Tyr Ala His Pro Ala Glu Ile Leu Phe Leu Gly
            180                 185                 190

Phe Ala Thr Val Val Gly Pro Ala Leu Thr Gly Pro His Leu Phe Thr
        195                 200                 205

Leu Trp Leu Trp Met Val Leu Arg Val Leu Glu Thr Val Glu Ala His
    210                 215                 220

Ser Gly Tyr His Phe Pro Trp Ser Pro Ser Asn Phe Leu Pro Leu Tyr
225                 230                 235                 240

Gly Gly Ser Asp Phe His Asp Tyr His His Arg Val Leu Tyr Thr Lys
                245                 250                 255

Ser Gly Asn Tyr Ala Ser Thr Phe Val Tyr Met Asp Trp Leu Phe Gly
            260                 265                 270
```

Thr Asp Lys Asp Tyr Arg Lys Ala Lys Thr Ile Glu Glu Lys Glu Gly
            275                 280                 285

Lys Asn Leu
        290

<210> SEQ ID NO 21
<211> LENGTH: 815
<212> TYPE: DNA
<213> ORGANISM: Oryza sativa

<400> SEQUENCE: 21
cacaattgtt ggtccggccc tcactggtcc gcacttgttc actctatggc tgtggatggt    60
gttgagggta ttggagacag ttgaagctca cagtggatac catttcccat ggagcccatc   120
aaatttcttg ccactgtatg gaggctccga ctttcatgac tatcatcacc gtgtgctcta   180
caccaaatca ggaaactacg cctctacttt tgtttacatg gactggctgt ttggcacgga   240
caaggattac cgcaatgcca aggctatcga ggagaaagac gggaagcatt tgtaaattgt   300
gggggctact ctctttctct tgtccaaat catcgaaaca agggtttgac atctcgcagt   360
ggtgatagca ttgtgttcat ggaggaaat aggtgtccta gccacaggta tctatctcct   420
gagatgatcc tacagtttag attttctttc cccaaattca ctatactatc atcatgagac   480
ctttgtgttt ctggaggcca ccatgatgta atttgtcata agcttaattt gatgcgtgct   540
attttgtggt ttgcttggac gggggtacat gccatgacag aagtgaacta ttcgaatcag   600
aaagttgtca gattagtgag ttaacgttaa aaaaaaaaaa aaaaaactc gaggcggggc   660
cagtaccaca attcgcgctc gtacccgggt ggtggtgatc aaattcggta tgactgacgt   720
ggttcgcggt cgtaggcatt gctatcaatg catcgcggct cacagtacga aagcaggag   780
ttagtttgtt gtccttaccg gcatcctagt actat                              815

<210> SEQ ID NO 22
<211> LENGTH: 97
<212> TYPE: PRT
<213> ORGANISM: Oryza sativa

<400> SEQUENCE: 22

Thr Ile Val Gly Pro Ala Leu Thr Gly Pro His Leu Phe Thr Leu Trp
 1               5                  10                  15

Leu Trp Met Val Leu Arg Val Leu Glu Thr Val Glu Ala His Ser Gly
             20                  25                  30

Tyr His Phe Pro Trp Ser Pro Ser Asn Phe Leu Pro Leu Tyr Gly Gly
         35                  40                  45

Ser Asp Phe His Asp Tyr His His Arg Val Leu Tyr Thr Lys Ser Gly
     50                  55                  60

Asn Tyr Ala Ser Thr Phe Val Tyr Met Asp Trp Leu Phe Gly Thr Asp
 65                  70                  75                  80

Lys Asp Tyr Arg Asn Ala Lys Ala Ile Glu Glu Lys Asp Gly Lys His
                 85                  90                  95

Leu

<210> SEQ ID NO 23
<211> LENGTH: 1192
<212> TYPE: DNA
<213> ORGANISM: Glycine max

<400> SEQUENCE: 23

-continued

```
gcacgaggca tccacttccc cactctctca catattgcct ctctctttcc tctttccatt      60
gtccatggcg tccctcatcg aatctggctg cagtacttg  atcacacatt tcagtgactt     120
tcaactggcg tgtttgggaa gtttcttcct acatgaaggc gttttcttct tgtctggact     180
tcccttata  tggcttgaga gggcagggtg gatgagcaag tacaaaattc aggccaaaaa     240
taacacccct gcagctcagg agaaatgtat tgttcgtctg ttgctttacc attttggtgt     300
caatctacct gttatgattt tttcatatcc tgtcttcaca tacatgggca tgcggagtag     360
tcttcccta  ccgtcctgga aagtagttct aattcaaata atcttttact tcattttgga     420
ggactttata ttctactggg gacatagaat actgcacaca aagtggttat acaagcatgt     480
gcacagtgtt catcatgagt atgctacacc gtttggattg acttctgaat atgctcatcc     540
tgctgagata cttttccttg gtttgctac  cattttggt  cctgccatta ctgggcccca     600
cttgataact ctctggttat ggatggttct gagagtccta gagacagttg aggctcattg     660
tggttaccat ttcccatgga gtctttccaa cttccttcca ttgtatggag gagctgattt     720
ccatgactat catcaccgtt tattgtacac caagtctggg aactattcat caacttttac     780
ttacatggac cggatatttg ggactgatat aggctacaga aagttgaaag cattgaagag     840
cataggagtt gaagacagtg gcgagcaaaa gaaacaataa gaatacgttt ttaggaatat     900
ccaggaatga ttagagagtt gatttgcaaa agggcatatt tgaaaaatgt ctatgatatc     960
aactccttat gtgttcttgt gtttttgtag tagctggtgt ttgtcttcaa tgtgctgatg    1020
gcttttctg  gacattcatg ccctgttatt agaaaaactt cattattgac agtaatttca    1080
attttgggat gtttcccttt gctgaaaaaa aaaaaaaaaa aaaaaaaaaa aaaaaaaaaa    1140
aaaaaaaaaa aagaaaaaaa aaaaaaaaaa aaaaaaaaaa aaaaatcccc cg            1192
```

<210> SEQ ID NO 24
<211> LENGTH: 292
<212> TYPE: PRT
<213> ORGANISM: Glycine max

<400> SEQUENCE: 24

```
His Glu Ala Ser Thr Ser Pro Leu Ser His Ile Leu Pro Leu Ser Phe
  1               5                  10                  15

Leu Phe Pro Leu Ser Met Ala Ser Leu Ile Glu Ser Gly Trp Gln Tyr
             20                  25                  30

Leu Ile Thr His Phe Ser Asp Phe Gln Leu Ala Cys Leu Gly Ser Phe
         35                  40                  45

Phe Leu His Glu Gly Val Phe Phe Leu Ser Gly Leu Pro Phe Ile Trp
     50                  55                  60

Leu Glu Arg Ala Gly Trp Met Ser Lys Tyr Lys Ile Gln Ala Lys Asn
 65                  70                  75                  80

Asn Thr Pro Ala Ala Gln Glu Lys Cys Ile Val Arg Leu Leu Leu Tyr
                 85                  90                  95

His Phe Gly Val Asn Leu Pro Val Met Ile Phe Ser Tyr Pro Val Phe
            100                 105                 110

Thr Tyr Met Gly Met Arg Ser Ser Leu Pro Leu Pro Ser Trp Lys Val
        115                 120                 125

Val Leu Ile Gln Ile Ile Phe Tyr Phe Ile Leu Glu Asp Phe Ile Phe
    130                 135                 140

Tyr Trp Gly His Arg Ile Leu His Thr Lys Trp Leu Tyr Lys His Val
145                 150                 155                 160

His Ser Val His His Glu Tyr Ala Thr Pro Phe Gly Leu Thr Ser Glu
```

```
                165                 170                 175
Tyr Ala His Pro Ala Glu Ile Leu Phe Leu Gly Phe Ala Thr Ile Phe
            180                 185                 190

Gly Pro Ala Ile Thr Gly Pro His Leu Ile Thr Leu Trp Leu Trp Met
        195                 200                 205

Val Leu Arg Val Leu Glu Thr Val Glu Ala His Cys Gly Tyr His Phe
    210                 215                 220

Pro Trp Ser Leu Ser Asn Phe Leu Pro Leu Tyr Gly Gly Ala Asp Phe
225                 230                 235                 240

His Asp Tyr His His Arg Leu Leu Tyr Thr Lys Ser Gly Asn Tyr Ser
                245                 250                 255

Ser Thr Phe Thr Tyr Met Asp Arg Ile Phe Gly Thr Asp Ile Gly Tyr
            260                 265                 270

Arg Lys Leu Lys Ala Leu Lys Ser Ile Gly Val Glu Asp Ser Gly Glu
        275                 280                 285

Gln Lys Lys Gln
        290
```

<210> SEQ ID NO 25
<211> LENGTH: 613
<212> TYPE: DNA
<213> ORGANISM: Triticum aestivum

<400> SEQUENCE: 25

```
gccagaccta gtcattgatt caccctctct cctaaagcct cttttaaagt tggggtggtg      60
ccagtggata ggtgctattg tattcatttg gggatccctc catcagatcc gttgtcatgc     120
aattcttgga tcgttgcgcg aaaataaaga ttctgatgaa tatgttattc cttgcggtga     180
ctggtttagt cgtgtgtctt gccctcatta ccttgctgaa ctagttatat atttgggcat     240
gttgatagct agtggtggat cagacatttc agtgtggttc ctgttcattt ttgtgataac     300
aaacttgtca tttgcagcag tacaaactca taggtggtac ctccaaaagt ttgaagacta     360
cccccgctct cgctatgcta tcattccatt tgtattgtag catctacaag cattccttct     420
gtgcagtaaa aatctgtgtg ttctggctag aatgcacaag cccggcatgt aaaagatatt     480
catgtaaatg tgacagcatg taagttaaaa tgttgtgttg tgtgacttga aatacttaca     540
agggttctat ttccagttgt aaattgcgat aaaaaaaaaa aaaaaaaact cgagggggggg    600
ccgtgcccaa tca                                                        613
```

<210> SEQ ID NO 26
<211> LENGTH: 132
<212> TYPE: PRT
<213> ORGANISM: Triticum aestivum

<400> SEQUENCE: 26

```
Pro Asp Leu Val Ile Asp Ser Pro Ser Leu Leu Lys Pro Leu Leu Lys
1               5                   10                  15

Leu Gly Trp Cys Gln Trp Ile Gly Ala Ile Val Phe Ile Trp Gly Ser
            20                  25                  30

Leu His Gln Ile Arg Cys His Ala Ile Leu Gly Ser Leu Arg Glu Asn
        35                  40                  45

Lys Asp Ser Asp Glu Tyr Val Ile Pro Cys Gly Asp Trp Phe Ser Arg
    50                  55                  60

Val Ser Cys Pro His Tyr Leu Ala Glu Leu Val Ile Tyr Leu Gly Met
65                  70                  75                  80
```

```
Leu Ile Ala Ser Gly Gly Ser Asp Ile Ser Val Trp Phe Leu Phe Ile
                85                  90                  95

Phe Val Ile Thr Asn Leu Ser Phe Ala Ala Val Gln Thr His Arg Trp
            100                 105                 110

Tyr Leu Gln Lys Phe Glu Asp Tyr Pro Arg Ser Arg Tyr Ala Ile Ile
        115                 120                 125

Pro Phe Val Leu
        130

<210> SEQ ID NO 27
<211> LENGTH: 991
<212> TYPE: DNA
<213> ORGANISM: Zea mays

<400> SEQUENCE: 27
gcacgagcat cgccgcgcac tcgggatcca acgtcgtcgg catcaccatc aacgagtacc      60
aggtgaaccg cgcccgcgcg cacaaccgca aggccggcct cgactcccg cgctgcgagg     120
tcgtctgcgg caacttcctc tccatgccgt tcccggacgc ctccttcgac ggcgcctact     180
ccatcgaggc cacctgccac gcgcccaggc tgcaggacgt gtacggcgag gtctaccgcg     240
tgctcaagcc ggggggactc tacgtctcct acgagtgggt caccaccccg ctgtaccgcg     300
ccgaggaccc ggaccacgtc gagtgcatcc acggcatcga gcgcggcgac gcgctcccgg     360
ggctccgccg ccaggacgag atcgcgtcca tcgccaagga ggtcggcttc gaggtgctca     420
aggagcagga ccttgcgctg cccccgcgc tgccctggtg gacgcgcctc aagatgggcc     480
gcatcgccta ctggcgcaac tccctcgtcg tccgcgtgct caccatgctc cgggtcgcgc     540
ccaagggcgt ctccgaggtg cacgagatgc tctacgagac cgcgcagcac ctcacccgcg     600
gcggcgagac cggcatcttc acgcccatgc acatggtgct cctccgcaag cccgccgccg     660
ccgcctccac cgaggaggcc aactagtgta agactacaca ccgccaccaa tcagttacta     720
ctcgcccacc gcaaggggga gaaaatgggg agggaggaaa aagatgcaag cagcagcagc     780
accagaggta agaagagcag gctaatcggc gacttgaaga agttacaaat tgatctatta     840
gagaagaaga tactactagg aacgatgctt ctctccgttt actctttcc ctgttcgtag      900
ctttgagttt taatttttgt ttttggtgg acggattgtt ccggggaggt cgaggttggg      960
atctaaattt attttcaatc ggtggggatc c                                    991

<210> SEQ ID NO 28
<211> LENGTH: 227
<212> TYPE: PRT
<213> ORGANISM: Zea mays

<400> SEQUENCE: 28

Thr Ser Ile Ala Ala His Ser Gly Ser Asn Val Val Gly Ile Thr Ile
 1               5                  10                  15

Asn Glu Tyr Gln Val Asn Arg Ala Arg Ala His Asn Arg Lys Ala Gly
            20                  25                  30

Leu Asp Ser Pro Arg Cys Glu Val Cys Gly Asn Phe Leu Ser Met
        35                  40                  45

Pro Phe Pro Asp Ala Ser Phe Asp Gly Ala Tyr Ser Ile Glu Ala Thr
    50                  55                  60

Cys His Ala Pro Arg Leu Gln Asp Val Tyr Gly Glu Val Tyr Arg Val
 65                  70                  75                  80

Leu Lys Pro Gly Gly Leu Tyr Val Ser Tyr Glu Trp Val Thr Thr Pro
                85                  90                  95
```

```
Leu Tyr Arg Ala Glu Asp Pro Asp His Val Cys Ile His Gly Ile
            100                 105                 110

Glu Arg Gly Asp Ala Leu Pro Gly Leu Arg Arg Gln Asp Glu Ile Ala
        115                 120                 125

Ser Ile Ala Lys Glu Val Gly Phe Glu Val Leu Lys Glu Gln Asp Leu
    130                 135                 140

Ala Leu Pro Pro Ala Leu Pro Trp Trp Thr Arg Leu Lys Met Gly Arg
145                 150                 155                 160

Ile Ala Tyr Trp Arg Asn Ser Leu Val Val Arg Val Leu Thr Met Leu
                165                 170                 175

Arg Val Ala Pro Lys Gly Val Ser Glu Val His Glu Met Leu Tyr Glu
            180                 185                 190

Thr Ala Gln His Leu Thr Arg Gly Gly Glu Thr Gly Ile Phe Thr Pro
        195                 200                 205

Met His Met Val Leu Leu Arg Lys Pro Ala Ala Ala Ser Thr Glu
    210                 215                 220

Glu Ala Asn
225

<210> SEQ ID NO 29
<211> LENGTH: 1369
<212> TYPE: DNA
<213> ORGANISM: Glycine max

<400> SEQUENCE: 29
gcacgaggta aaacctcaca atcacaaaca cactctttt tgttctttgc tcacttccct      60
tgttcgtttc actctcacaa tggactccct ctctctcttc tgcaccggag cccttctcgc    120
cggcggcctc tactggttcg tctgtgttct gggccccgcc gagcagaagg gcaaacgcgc    180
caccgatcta tccggcggct ccatctccgc cgagaaagtc caagacaact acaagcagta    240
ctggtccttc ttccgccgcc ccaaggagat cgagaccgcc gacaaagttc ccgacttcgt    300
cgacaccttc tacaatctag tcaccgacat ctacgagtgg ggctggggcc agtccttcca    360
cttctccccc tccatccccg gtaagtccca ccgcgaggcc acgcgcctcc acgaggagat    420
ggccgtcgat ctcatcgagg ccaagcccgg caacaaaatc ctggacgtgg gctgcggcgt    480
gggcgggccc atgcgggcca tcgcggccca ctcccgcgcg aacgtggtgg gcatcaccat    540
caacgagtac caggtcaatc gagcaaggat gcacaacaag aaggctgggt tggactctct    600
ctgcgaggtc gtgtgtggga atttccttaa gatgccgttt gtcgacaaca gcttcgacgg    660
agcgtactcc atcgaggcca cgtgtcacgc tcccaagctg gaagaagtgt acgccgaaat    720
cttccgagtt ctgaaaccgg ggcgctcta cgtttcctac gagtgggtga cgacggataa    780
gtacagcggc gatgaccctg aacacgtgga ggtcattcag gggattgaga ggggtgacgc    840
gttgcctggc ctcagaagct acgccgaaat agccgaaacg cgcgtaaggt agggtttgc    900 tgttgtgaag gagcgggatc tggccaagcc gccggctctt ccctggtgga gccgattgaa    960
gatgggtagg atcgcgtact ggcggaacca tattgtggtc actgttctcg ccgctttggg   1020
aatcgcgcct aaggggaccg tcgatgttca tgagatgctc ttcaagaccg ctgactattt   1080
gaccagaggg ggtgactctg ggattttctc tccgatgcac atgatcctct gcagaaagcc   1140
ccatgacaag gacgaacaaa actctggtta gggtttcgtt tcatttggaa attggaaaac   1200
aaaaaccacc accgccacct tgtttctttc cggtactctt ttttctcatt attatcctgg   1260
gtttaacttg ttgttattag ttattattac tatgaacttg gtgtaatttg gattttgatc   1320
```
ttttcaattt taattttagt ttgcaatgtt aaaaaaaaaa aaaaaaaaa    1369

<210> SEQ ID NO 30
<211> LENGTH: 361
<212> TYPE: PRT
<213> ORGANISM: Glycine max

<400> SEQUENCE: 30

```
Met Asp Ser Leu Ser Leu Phe Cys Thr Gly Ala Leu Leu Ala Gly Gly
 1               5                  10                  15

Leu Tyr Trp Phe Val Cys Val Leu Gly Pro Ala Glu Gln Lys Gly Lys
                20                  25                  30

Arg Ala Thr Asp Leu Ser Gly Gly Ser Ile Ser Ala Glu Lys Val Gln
            35                  40                  45

Asp Asn Tyr Lys Gln Tyr Trp Ser Phe Phe Arg Arg Pro Lys Glu Ile
        50                  55                  60

Glu Thr Ala Asp Lys Val Pro Asp Phe Val Asp Thr Phe Tyr Asn Leu
 65                  70                  75                  80

Val Thr Asp Ile Tyr Glu Trp Gly Trp Gly Gln Ser Phe His Phe Ser
                85                  90                  95

Pro Ser Ile Pro Gly Lys Ser His Arg Glu Ala Thr Arg Leu His Glu
            100                 105                 110

Glu Met Ala Val Asp Leu Ile Glu Ala Lys Pro Gly Asn Lys Ile Leu
        115                 120                 125

Asp Val Gly Cys Gly Val Gly Gly Pro Met Arg Ala Ile Ala Ala His
    130                 135                 140

Ser Arg Ala Asn Val Val Gly Ile Thr Ile Asn Glu Tyr Gln Val Asn
145                 150                 155                 160

Arg Ala Arg Met His Asn Lys Lys Ala Gly Leu Asp Ser Leu Cys Glu
                165                 170                 175

Val Val Cys Gly Asn Phe Leu Lys Met Pro Phe Val Asp Asn Ser Phe
            180                 185                 190

Asp Gly Ala Tyr Ser Ile Glu Ala Thr Cys His Ala Pro Lys Leu Glu
        195                 200                 205

Glu Val Tyr Ala Glu Ile Phe Arg Val Leu Lys Pro Gly Ala Leu Tyr
    210                 215                 220

Val Ser Tyr Glu Trp Val Thr Thr Asp Lys Tyr Ser Gly Asp Pro
225                 230                 235                 240

Glu His Val Glu Val Ile Gln Gly Ile Glu Arg Gly Asp Ala Leu Pro
                245                 250                 255

Gly Leu Arg Ser Tyr Ala Glu Ile Ala Glu Thr Ala Arg Lys Val Gly
            260                 265                 270

Phe Ala Val Val Lys Glu Arg Asp Leu Ala Lys Pro Ala Leu Pro
        275                 280                 285

Trp Trp Ser Arg Leu Lys Met Gly Arg Ile Ala Tyr Trp Arg Asn His
    290                 295                 300

Ile Val Val Thr Val Leu Ala Ala Leu Gly Ile Ala Pro Lys Gly Thr
305                 310                 315                 320

Val Asp Val His Glu Met Leu Phe Lys Thr Ala Asp Tyr Leu Thr Arg
                325                 330                 335
```

```
                                -continued

Gly Gly Asp Ser Gly Ile Phe Ser Pro Met His Met Ile Leu Cys Arg
            340                 345             350

Lys Pro His Asp Lys Asp Glu Gln Asn
        355             360
```

US 6,479,733 B1

STEROL METABOLISM ENZYMES

This application claims priority benefit of U.S. Provisional Application No. 60/108,351 filed Nov. 13, 1998, now pending.

FIELD OF THE INVENTION

This invention is in the field of plant molecular biology. More specifically, this invention pertains to nucleic acid fragments encoding enzymes involved in sterol metabolism in plants and seeds.

BACKGROUND OF THE INVENTION

Sterols play major roles in plant growth and development. C-4 methyl sterol oxidase (methyl sterol oxidase) catalyzes the-first of three enzymatic steps in the removal of the two C-4 methyl groups of 4,4-dimethylzymosterol leading to cholesterol (animal), ergosterol (fungal), and stigmasterol (plant) biosynthesis. The yeast methyl sterol oxidase ERG25 and its human homologue contain a putative set of metal binding motifs with similarity to that seen in a family of membrane desaturases-hydroxylases. The C-4 methyl sterol oxidase is regulated not by iron but by an end product of the ergosterol pathway, and changes to its activity result in marked changes in lipid metabolism, including the accumulation of fatty acids, triglycerides, methyl sterols, and other sterol precursors (Li and Kaplan (1996) *J. Biol. Chem.* 271:16927–16933).

In plants, the dominant sterols are 24-alkyl sterols, which play multiple roles in plant growth and development, i.e. as membrane constituents and as precursors to steroid growth regulators such as brassinosteroids. The initial step in the conversion of the phytosterol intermediate cycloartenol to the 24-alkyl sterols is catalyzed by S-adenosyl-L-methionine:delta 24-sterol-C-methyl-transferase, a rate-limiting enzyme for phytosterol biosynthesis. The gene encoding the soybean 24-sterol-C-methyl transferase has been identified and is similar to the yeast ERG6 gene. Higher levels of 24-sterol-C-methyl transferase transcript are found in higher abundance in growing vegetative tissues than in mature vegetative tissues. This transcript is highly expressed in flowers and present in very small amounts in young pods and immature seeds (Shi et al. (1996) *J. Biol. Chem.* 271:9384–9389). At least two methyl transferases have been identified in *Arabidopsis thaliana*, two in *Nicotiana tabacum*, and one in *Ricinus communis* (Bouvier-Nave et al. (1997) *Eur. J Biochem.* 246:518–529).

Brassinosteroids are ubiquitously distributed in the plant kingdom, and when applied exogenously at nanomolar to micromolar levels, they exhibit a wide spectrum of physiological effects including promotion of cell elongation and division, enhancement of tracheary element differentiation, retardation of abscission, enhancement of gravitropic-induced bending, promotion of ethylene biosynthesis, and enhancement of stress resistance. The Arabidopsis DEETIOLATED2 (DET2) catalyzes the formation of campestanol from campesterol in brassinosteroid biosynthesis (Fujioka et al (1997) *Plant Cell* 9:1951–1962). DET2 is a steroid 5-alpha reductase with biochemical properties similar to the mammalian enzyme which is also called 3-oxo-5-alpha steroid 4-dehydrogenase (EC 1.3.99.5).

Sequences of ESTs which may encode portions of C-4 methyl sterol oxidase are found in the NCBI database having General Identifier Nos. 5069775, 4966861, 4966892, and 6031650. EST sequences which may encode sterol-c-methyl transferases are found in the NCBI database having General Identifier Nos. 5509139, 5753639, 4313622, 5820099, 6070142, and 6070563.

Elucidation of all the genes involved in sterol metabolism will allow the manipulation of the oil and protein content of the grains.

SUMMARY OF THE INVENTION

The present invention relates to an isolated polynucleotide comprising the nucleotide sequence comprising at least 30 contiguous nucleotides of a nucleic acid sequence selected from the group consisting of SEQ ID NOs:1, 3, 5, 7, 9, 11, 13, 15,17, 19, 21, 23, 25, 27, and 29 or compositions thereof.

The present invention relates to an expression cassette comprising an isolated polynucleotide of the present invention operably linked to a promoter.

The present invention relates to isolated polynucleotides comprising a nucleotide sequence encoding a first polypeptide of at least 200 amino acids that has at least 95% identity based on the Clustal method of alignment when compared to a polypeptide selected from the group consisting of a corn C-4 methyl sterol oxidase polypeptide of SEQ ID NO:20. The present invention relates to isolated polynucleotides comprising a nucleotide sequence encoding a first polypeptide of at least 90 amino acids that has at least 85% identity based on the Clustal method of alignment when compared to a polypeptide selected from the group consisting of a rice C-4 methyl sterol oxidase polypeptide of SEQ ID NO:22, a soybean C-4 methyl sterol oxidase polypeptide of SEQ ID NO:24, a wheat C-4 methyl sterol oxidase polypeptide of SEQ ID NO:8. The present invention also relates to an isolated polynucleotide comprising the complement of the nucleotide sequences described above.

The present invention relates to isolated polynucleotides comprising a nucleotide sequence encoding a first polypeptide of at least 70 amino acids that has at least 80% identity based on the Clustal method of alignment when compared to a polypeptide selected from the group consisting of a corn steroid 5alpha-reductase polypeptide of SEQ ID NO:10. The present invention relates to isolated polynucleotides comprising a nucleotide sequence encoding a first polypeptide of at least 120 amino acids that has at least 80% identity based on the Clustal method of alignment when compared to a polypeptide a wheat steroid 5alpha-reductase polypeptide of SEQ ID NO:26. The present invention also relates to an isolated polynucleotide comprising the complement of the nucleotide sequences described above.

The present invention relates to isolated polynucleotides comprising a nucleotide sequence encoding a first polypeptide of at least 90 amino acids that has at least 95% identity based on the Clustal method of alignment when compared to a polypeptide selected from the group consisting of a corn sterol-c-methyl transferase polypeptide of SEQ ID NO:28, and a rice sterol-c-methyl transferase polypeptide of SEQ ID NO:16. The present invention relates to isolated polynucleotides comprising a nucleotide sequence encoding a first polypeptide of at least 220 amino acids that has at least 95% identity based on the Clustal method of alignment when compared to a polypeptide selected from the group consisting of a soybean sterol-c-methyl transferase polypeptide of SEQ ID NO:30. The present invention also relates to an isolated polynucleotide comprising the complement of the nucleotide sequences described above.

It is preferred that the isolated polynucleotides of the claimed invention consist of a nucleic acid sequence selected from the group consisting of SEQ ID NOs:1, 3, 5, 7, 9, 11, 13, 15, 17, 19, 21, 23, 25, 27, and 29 that codes for the polypeptide selected from the group consisting of SEQ ID NOs:2, 4, 6, 8,10, 12, 14, 16, 18, 20, 22, 24, 26, 28, and 30. The present invention also relates to an isolated polynucleotide comprising a nucleotide sequences of at least 30 (preferably at least 40, most preferably at least 60) contiguous nucleotide derived from a nucleotide sequence selected from the group consisting of SEQ ID NOs. 3, 5, 7, 9, 11, 13, 15, 17, 19, 21, 23, 25, 27, 29, and the complement of such nucleotide sequences.

The present invention relates to a chimeric gene comprising an isolated polynucleotide of the present invention operably linked to suitable regulatory sequences.

The present invention relates to an isolated host cell comprising a chimeric gene of the present invention or an isolated polynucleotide of the present invention. The host cell may be eukaryotic, such as a yeast or a plant cell, or prokaryotic, such as a bacterial cell. The present invention also relates to a virus, preferably a baculovirus, comprising an isolated polynucleotide of the present invention or a chimeric gene of the present invention.

The present invention relates to a process for producing an isolated host cell comprising a chimeric gene of the present invention or an isolated polynucleotide of the present invention, the process comprising either transforming or transfecting an isolated compatible host cell with a chimeric gene or isolated polynucleotide of the present invention.

The present invention relates to a C-4 methyl sterol oxidase polypeptide of at least 200 amino acids comprising at least 95% homology based on the Clustal method of alignment compared to a polypeptide from SEQ ID NO:20.

The present invention relates to a C-4 methyl sterol oxidase polypeptide of at least 90 amino acids comprising at least 85% homology based on the Clustal method of alignment compared to a polypeptide of SEQ ID NO:22.

The present invention relates to a C-4 methyl sterol oxidase polypeptide of at least 90 amino acids comprising at least 85% homology based on the Clustal method of alignment compared to a polypeptide of SEQ ID NO:24.

The present invention relates to a C-4 methyl sterol oxidase polypeptide of at least 90 amino acids comprising at least 85% homology based on the Clustal method of alignment compared to a polypeptide of SEQ ID NO:8.

The present invention relates to a steroid 5-alpha reductase polypeptide of at least 70 amino acids comprising at least 80% homology based on the Clustal method of alignment compared to a polypeptide of SEQ ID NO:10.

The present invention relates to a steroid 5-alpha reductase polypeptide of at least 120 amino acids comprising at least 80% homology based on the Clustal method of alignment compared to a polypeptide of SEQ ID NO:26.

The present invention relates to a sterol C-methyl transferase polypeptide of at least 90 amino acids comprising at least 95% homology based on the Clustal method of alignment compared to a polypeptide selected from the group consisting of SEQ ID NOs:28 and 16.

The present invention relates to C-4 methyl transferase polypeptide of at least 220 amino acids comprising at least 95% homology based on the Clustal method of alignment compared to a polypeptide of SEQ ID NO:30.

The present invention relates to a method of selecting an isolated polynucleotide that affects the level of expression of a C-4 methyl sterol oxidase, a steroid 5-alpha reductase, or a sterol c-methyl transferase polypeptide in a host cell, preferably a plant cell, the method comprising the steps of:

constructing an isolated polynucleotide of the present invention or an isolated chimeric gene of the present invention;

introducing the isolated polynucleotide or the isolated chimeric gene into a host cell;

measuring the level a C-4 methyl sterol oxidase, a steroid 5-alpha reductase, or a sterol c-methyl transferase polypeptide in the host cell containing the isolated polynucleotide; and comparing the level of a C-4 methyl sterol oxidase, a steroid 5-alpha reductase, or a sterol c-methyl transferase polypeptide in the host cell containing the isolated polynucleotide with the level of a C-4 methyl sterol oxidase, a steroid 5-alpha reductase, or a sterol c-methyl transferase polypeptide in a host cell that does not contain the isolated polynucleotide.

The present invention relates to a method of obtaining a nucleic acid fragment encoding a substantial portion of a C-4 methyl sterol oxidase, a steroid 5-alpha reductase, or a sterol c-methyl transferase polypeptide gene, preferably a plant C-4 methyl sterol oxidase, steroid 5-alpha reductase, or sterol c-methyl transferase polypeptide gene, comprising the steps of: synthesizing an oligonucleotide primer comprising a nucleotide sequence of at least 30 (preferably at least 40) contiguous nucleotides derived from a nucleotide sequence selected from the group consisting of SEQ ID NOs:1, 3, 5, 7, 9, 11, 13, 15, 17, 19, 21, 23, 25, 27, 29, and the complement of such nucleotide sequences; and amplifying a nucleic acid fragment (preferably a cDNA inserted in a cloning vector) using the oligonucleotide primer. The amplified nucleic acid fragment preferably will encode a portion of a C-4 methyl sterol oxidase, a steroid 5-alpha reductase, or a sterol c-methyl transferase amino acid sequence.

The present invention also relates to a method of obtaining a nucleic acid fragment encoding all or a substantial portion of the amino acid sequence encoding a C-4 methyl sterol oxidase, a steroid 5-alpha reductase, or a sterol c-methyl transferase polypeptide comprising the steps of: probing a cDNA or genomic library with an isolated polynucleotide of the present invention; identifying a DNA clone that hybridizes with an isolated polynucleotide of the present invention; isolating the identified DNA clone; and sequencing the cDNA or genomic fragment that comprises the isolated DNA clone.

A further embodiment of the instant invention is a method for evaluating at least one compound for its ability to inhibit the activity of a C-4 methyl sterol oxidase, a steroid 5-alpha reductase, or a sterol c-methyl transferase, the method comprising the steps of: (a) transforming a host cell with a chimeric gene comprising a nucleic acid fragment encoding a C-4 methyl sterol oxidase, a steroid 5-alpha reductase, or a sterol c-methyl transferase, operably linked to suitable regulatory sequences; (b) growing the transformed host cell under conditions that are suitable for expression of the chimeric gene wherein expression of the chimeric gene results in production of C-4 methyl sterol oxidase, steroid 5-alpha reductase, or sterol c-methyl transferase in the transformed host cell; (c) optionally purifying the C-4 methyl sterol oxidase, steroid 5-alpha reductase, or sterol c-methyl transferase expressed by the transformed host cell; (d) treating the C-4 methyl sterol oxidase, steroid 5-alpha reductase, or sterol c-methyl transferase with a compound to be tested; and (e) comparing the activity of the C-4 methyl sterol oxidase, steroid 5-alpha reductase, or sterol c-methyl transferase that has been treated with a test compound to the activity of an untreated C-4 methyl sterol oxidase, steroid 5-alpha reductase, or sterol c-methyl transferase, thereby selecting compounds with potential for inhibitory activity.

The present invention relates to a method for positive selection of a transformed cell comprising:

(a) transforming a plant cell, such as a monocot or dicot like corn, rice, wheat, or soy, with an expression cassette of the present invention or a chimeric gene of the present invention; and (b) growing the transformed plant cell under conditions allowing expression of the polynucleotide in an amount sufficient to complement a sterol metabolism enzyme auxotroph in a plant cell to provide a positive selection means.

As used herein, the following terms shall apply:

"Sterol metabolism enzyme" refers to C4 methyl sterol oxidase, steroid 5-alpha reductase, and/or sterol-c-methyltransferase.

BRIEF DESCRIPTION OF THE SEQUENCE LISTING

The invention can be more fully understood from the following detailed description and the accompanying Sequence Listing which form a part of this application.

Table 1 lists the polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence Listing. The sequence descriptions and Sequence Listing attached hereto comply with the rules governing nucleotide and/or amino acid sequence disclosures in patent applications as set forth in 37 C.F.R. §1.821–1.825.

TABLE 1

Enzymes Involved in Sterol Metabolism

| | | SEQ ID NO: | |
| --- | --- | --- | --- |
| Protein | Clone Designation | (Nucleotide) | (Amino Acid) |
| Corn C-4 Methyl Sterol Oxidase | cen3-bs.pk0018.a4 | 1 | 2 |
| Rice C-4 Methyl Sterol Oxidase | rr1.pk0074.e3 | 3 | 4 |
| Soybean C-4 Methyl Sterol Oxidase | Contig of: sgs2c.pk004.d12 sf11.pk0070.a9 | 5 | 6 |
| Wheat C-4 Methyl Sterol Oxidase | Contig of: wre1n.pk0057.d11 wle1n.pk0054.a2 | 7 | 8 |
| Corn Steroid 5-Alpha Reductase | cen3n.pk0129.d6 | 9 | 10 |
| Wheat Steroid 5-Alpha Reductase | wle1n.pk0043.b1 | 11 | 12 |
| Corn Sterol-C-Methyl Transferase | cr1.pk0029.d11 | 13 | 14 |
| Rice Sterol-C-Methyl Transferase | rr1.pk0045.b9 | 15 | 16 |
| Soybean Steorol-C-Methyl Transferase | Contig of: sgs5c.pk0003.f9 src2c.pk001.o5 sdc1c.pk0004.b11 sr1.pk0018.g3 | 17 | 18 |
| Corn C-4 Methyl Sterol Oxidase | cen3-bs.pk0018.a4:fis | 19 | 20 |
| Rice C-4 Methyl Sterol Oxidase | rr1.pk0074.e3:fis | 21 | 22 |
| Soybean C-4 Methyl Sterol Oxidase | sgs2c.pk004.d12:fis | 23 | 24 |
| Wheat Steroid 5-Alpha Reductase | wle1n.pk0043.b1:fis | 25 | 26 |
| Corn Sterol-C-Methyl Transferase | cr1.pk0029.d11:fis | 27 | 28 |
| Soybean Sterol-C-Methyl Transferase | sr1.pk0018.g3:fis | 29 | 30 |

The Sequence Listing contains the one letter code for nucleotide sequence characters and the three letter codes for amino acids as defined in conformity with the IUPAC-IUBMB standards described in *Nucleic Acids Res.* 13:3021–3030 (1985) and in the *Biochemical J.* 219 (No. 2):345–373 (1984) which are herein incorporated by reference. The symbols and format used for nucleotide and amino acid sequence data comply with the rules set forth in 37 C.F.R. §1.822.

DETAILED DESCRIPTION OF THE INVENTION

In the context of this disclosure, a number of terms shall be utilized. As used herein, a "polynucleotide" is a nucleotide sequence such as a nucleic acid fragment. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, or synthetic DNA. An isolated polynucleotide of the present invention may include at least 30 contiguous nucleotides, preferably at least 40 contiguous nucleotides, most preferably at least 60 contiguous nucleotides, of the nucleic acid sequence of the SEQ ID NOs:1, 3, 5, 7, 9, 11, 13, 15, 17, 19,21,23,25,27, and 29.

As used herein, "contig" refers to a nucleotide sequence that is assembled from two or more constituent nucleotide sequences that share common or overlapping regions of sequence homology. For example, the nucleotide sequences of two or more nucleic acid fragments can be compared and aligned in order to identify common or overlapping sequences. Where common or overlapping sequences exist between two or more nucleic acid fragments, the sequences (and thus their corresponding nucleic acid fragments) can be assembled into a single contiguous nucleotide sequence.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to nucleic acid fragments wherein changes in one or more nucleotide bases does not affect the ability of the nucleic acid fragment to mediate alteration of gene expression by gene silencing through for example antisense or co-suppression technology. "Substantially similar" also refers to modifications of the nucleic acid fragments of the instant invention such as deletion or insertion of one or more nucleotides that do not substantially affect the functional properties of the resulting transcript vis-a-vis the ability to mediate gene silencing or alteration of the functional properties of the resulting protein molecule. It is therefore understood that the invention encompasses more than the specific exemplary nucleotide or amino acid sequences and includes functional equivalents thereof.

Substantially similar nucleic acid fragments may be selected by screening nucleic acid fragments representing subfragments or modifications of the nucleic acid fragments of the instant invention, wherein one or more nucleotides are substituted, deleted and/or inserted, for their ability to affect the level of the polypeptide encoded by the unmodified nucleic acid fragment in a plant or plant cell. For example, a substantially similar nucleic acid fragment representing at least 30 contiguous nucleotides derived from the instant nucleic acid fragment can be constructed and introduced into a plant or plant cell. The level of the polypeptide encoded by the unmodified nucleic acid fragment present in a plant or plant cell exposed to the substantially similar nucleic fragment can then be compared to the level of the polypeptide in a plant or plant cell that is not exposed to the substantially similar nucleic acid fragment.

For example, it is well known in the art that antisense suppression and co-suppression of gene expression may be accomplished using nucleic acid fragments representing less than the entire coding region of a gene, and by nucleic acid fragments that do not share 100% sequence identity with the gene to be suppressed. Moreover, alterations in a nucleic acid fragment which result in the production of a chemically equivalent amino acid at a given site, but do not effect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. Consequently, an isolated polynucleotide comprising a nucleotide sequence of at least 30 (preferably at least 40, most preferably at least 60) contiguous nucleotides derived from a nucleotide sequence selected from the group consisting of SEQ ID NOs:1, 3, 5, 7, 9, 11, 13, 15, 17, 19, 21, 23, 25, 27, and 29 and the complement of such nucleotide sequences may be used in methods of selecting an isolated polynucleotide that affects the expression of a polypeptide in a plant cell. A method of selecting an isolated polynucleotide that affects the level of expression of a polypeptide (such as a sterol metabolism enzyme) in a host cell (eukaryotic, such as plant or yeast, prokaryotic such as bacterial, or viral) may comprise the steps of: constructing an isolated polynucleotide of the present invention or an isolated chimeric gene of the present invention; introducing the isolated polynucleotide or the isolated chimeric gene into a host cell; measuring the level of a polypeptide in the host cell containing the isolated polynucleotide; and comparing the level of a polypeptide in the host cell containing the isolated polynucleotide with the level of a polypeptide in a host cell that does not contain the isolated polynucleotide.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (Hames and Higgins, Eds. (1985) Nucleic Acid Hybridisation, IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C.

Substantially similar nucleic acid fragments of the instant invention may also be characterized by the percent identity of the amino acid sequences that they encode to the amino acid sequences disclosed herein, as determined by algorithms commonly employed by those skilled in this art. Suitable nucleic acid fragments (isolated polynucleotides of the present invention) encode polypeptides that are at least 70% identical, preferably at least 80% identical to the amino acid sequences reported herein. Preferred nucleic acid fragments encode amino acid sequences that are at least 85% identical to the amino acid sequences reported herein. More preferred nucleic acid fragments encode amino acid sequences that are at least 90% identical to the amino acid sequences reported herein. Most preferred are nucleic acid fragments that encode amino acid sequences that are at least 95% identical to the amino acid sequences reported herein. Suitable nucleic acid fragments not only have the above homologies but typically encode a polypeptide having at least 50 amino acids, preferably at least 100 amino acids, more preferably at least 150 amino acids, still more preferably at least 200 amino acids, and most preferably at least 250 amino acids. Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) CABIOS. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul et al. (1993) J. Mol. Biol. 215:403–410). In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without affecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or finctional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of Plants* 15:1–82. It is further recognized that since in most cases the exact boundaries of regulatory sequences have not been completely defined, nucleic acid fragments of different lengths may have identical promoter activity.

The "translation leader sequence" refers to a nucleotide sequence located between the promoter sequence of a gene and the coding sequence. The translation leader sequence is present in the fully processed MRNA upstream of the translation start sequence. The translation leader sequence may affect processing of the primary transcript to mRNA, mRNA stability or translation efficiency. Examples of translation leader sequences have been described (Turner and Foster (1995) *Mol. Biotechnol.* 3:225–236).

The "3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the MRNA precursor. The use of different 3' non-coding sequences is exemplified by Ingelbrecht et al. (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into polypeptide by the cell. "cDNA" refers to a double-stranded DNA that is complementary to and derived from MRNA. "Sense" RNA refers to an RNA transcript that includes the MRNA and so can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

"Altered levels" refers to the production of gene product (s) in transgenic organisms in amounts or proportions that differ from that of normal or non-transformed organisms.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) *Ann. Rev. Plant Phys. Plant Mol. Biol.* 42:21–53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627–1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include Agrobacterium-mediated transformation (De Blaere et al. (1987) *Meth. Enzymol.* 143:277) and particle-accelerated or "gene gun" transformation technology (Klein et al. (1987) *Nature* (London) 327:70–73; U.S. Pat. No. 4,945,050, incorporated herein by reference).

Standard recombinant DNA and molecular cloning techniques used herein are well known in the art and are described more fully in Sambrook et al. *Molecular Cloning: A Laboratory Manual*; Cold Spring Harbor Laboratory Press: Cold Spring Harbor, 1989 (hereinafter "Maniatis").

Nucleic acid fragments encoding at least a portion of several sterol metabolism enzymes have been isolated and identified by comparison of random plant cDNA sequences to public databases containing nucleotide and protein sequences using the BLAST algorithms well known to those skilled in the art. The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other C-4 methyl sterol oxidases, steroid 5alpha-reductases, or sterol-c-methyl transferases, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, the entire sequences can be used directly to synthesize DNA probes by methods known to the skilled artisan such as random primer DNA labeling, nick translation, or end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al. (1988) *Proc. Natl. Acad. Sci. USA* 85:8998–9002) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al. (1989) *Proc. Natl. Acad Sci. USA* 86:5673–5677; Loh et al. (1989) *Science* 243:217–220). Products generated by the 3' and 5' RACE procedures can be combined to generate full-length cDNAs (Frohman and Martin (1989) *Techniques* 1:165). Consequently, a polynucleotide comprising a nucleotide sequence of at least 60 (preferably at least 40, most preferably at least 30) contiguous nucleotides derived from a nucleotide sequence selected from the group consisting of SEQ ID NOs:1, 3, 5, 7, 9, 11, 13, 15, 17, 19, 21, 23, 25, 27, and 29 and the complement of such nucleotide sequences may be used in such methods to obtain a nucleic acid fragment encoding a substantial portion of an amino acid sequence of a polypeptide. The present invention relates to a method of obtaining a nucleic acid fragment encoding a substantial portion of a polypeptide of a gene (such as C-4 methyl sterol oxidase, steroid 5alpha-reductase, or sterol-c-methyl transferase) preferably a substantial portion of a plant polypeptide of a gene, comprising the steps of: synthesizing an oligonucleotide primer comprising a nucleotide sequence of at least 30 (preferably at least 40, most preferably at least 60) contiguous nucleotides derived from a nucleotide sequence selected from the group consisting of SEQ ID NOs:1, 3, 5, 7, 9, 11, 13, 15, 17, 19, 21, 23, 25, 27, and 29, and the complement of such nucleotide sequences; and amplifying a nucleic acid fragment (preferably a cDNA inserted in a cloning vector) using the oligonucleotide primer. The amplified nucleic acid fragment preferably will encode a portion of a polypeptide.

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner (1984) *Adv. Immunol.* 36:1–34; Maniatis).

The nucleic acid fragments of the instant invention may be used to create transgenic plants in which the disclosed polypeptides are present at higher or lower levels than normal or in cell types or developmental stages in which they are not normally found. This would have the effect of altering the level of sterol biosynthesis in those cells. Overexpression of any one of these proteins will result in increase of oil and protein yield in plants. Changes in the expression levels of C-4 methyl sterol oxidase or sterol c-methyl transferase will alter the composition or relative levels of phytosterols in the kernels and oils. Increase in steroid 5-alpha reductase may result in growth stimulation.

Overexpression of the proteins of the instant invention may be accomplished by first constructing a chimeric gene in which the coding region is operably linked to a promoter capable of directing expression of a gene in the desired tissues at the desired stage of development. For reasons of convenience, the chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

Plasmid vectors comprising the instant chimeric gene can then be constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al. (1985) *EMBO J.* 4:2411–2418; De Almeida et al. (1989) *Mol. Gen. Genetics* 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant polypeptides to different cellular compartments, or to facilitate their secretion from the cell. It is thus envisioned that the chimeric gene described above may be further supplemented by altering the coding sequence to encode the instant polypeptides with appropriate intracellular targeting sequences such as transit sequences (Keegstra (1989) *Cell* 56:247–253), signal sequences or sequences encoding endoplasmic reticulum localization (Chrispeels (1991) *Ann. Rev. Plant Phys. Plant Mol. Biol.* 42:21–53), or nuclear localization signals (Raikhel (1992) *Plant Phys.* 100:1627–1632) added and/or with targeting sequences that are already present removed. While the references cited give examples of each of these, the list is not exhaustive and more targeting signals of utility may be discovered in the future.

It may also be desirable to reduce or eliminate expression of genes encoding the instant polypeptides in plants for some applications. In order to accomplish this, a chimeric gene designed for co-suppression of the instant polypeptide can be constructed by linking a gene or gene fragment encoding that polypeptide to plant promoter sequences. Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or cosuppression (U.S. Pat. Nos. 5,190,931, 5,107,065 and 5,283,323). An antisense or cosuppression construct would act as a dominant negative regulator of gene activity. While conventional mutations can yield negative regulation of gene activity these effects are most likely recessive. The dominant negative regulation available with a transgenic approach may be advantageous from a breeding perspective. In addition, the ability to restrict the expression of specific phenotype to the reproductive tissues of the plant by the use of tissue specific promoters may confer agronomic advantages relative to conventional mutations which may have an effect in all tissues in which a mutant gene is ordinarily expressed.

The person skilled in the art will know that special considerations are associated with the use of antisense or cosuppression technologies in order to reduce expression of particular genes. For example, the proper level of expression of sense or antisense genes may require the use of different chimeric genes utilizing different regulatory elements known to the skilled artisan. Once transgenic plants are obtained by one of the methods described above, it will be necessary to screen individual transgenics for those that most effectively display the desired phenotype. Accordingly, the skilled artisan will develop methods for screening large numbers of transformants. The nature of these screens will generally be chosen on practical grounds, and is not an inherent part of the invention. For example, one can screen by looking for changes in gene expression by using antibodies specific for the protein encoded by the gene being suppressed, or one could establish assays that specifically measure enzyme activity. A preferred method will be one which allows large numbers of samples to be processed rapidly, since it will be expected that a large number of transformants will be negative for the desired phenotype.

The instant polypeptides (or portions thereof) may be produced in heterologous host cells, particularly in the cells of microbial hosts, and can be used to prepare antibodies to the these proteins by methods well known to those skilled in the art. The antibodies are useful for detecting the polypeptides of the instant invention in situ in cells or in vitro in cell extracts. Preferred heterologous host cells for production of the instant polypeptides are microbial hosts. Microbial expression systems and expression vectors containing regulatory sequences that direct high level expression of foreign proteins are well known to those skilled in the art. Any of these could be used to construct a chimeric gene for production of the instant polypeptides. This chimeric gene could then be introduced into appropriate microorganisms via transformation to provide high level expression of the encoded sterol metabolism enzyme. An example of a vector for high level expression of the instant polypeptides in a bacterial host is provided (Example 8).

Additionally, the instant polypeptides can be used as targets to facilitate design and/or identification of inhibitors of those enzymes that may be useful as herbicides. This is desirable because the polypeptides described herein catalyze various steps in sterol metabolism. Accordingly, inhibition of the activity of one or more of the enzymes described herein could lead to inhibition of plant growth. Thus, the instant polypeptides could be appropriate for new herbicide discovery and design.

All or a substantial portion of the nucleic acid fragments of the instant invention may also be used as probes for genetically and physically mapping the genes that they are a part of, and as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al. (1987) *Genomics* 1:174–181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. (1980) *Am. J Hum. Genet.* 32:314–331).

The production and use of plant gene-derived probes for use in genetic mapping is described in Bernatzky and Tanksley (1986) *Plant Mol. Biol. Reporter* 4:37–41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al. In: *Nonmammalian Genomic Analysis: A Practical Guide*, Academic press 1996, pp. 319–346, and references cited therein).

In another embodiment, nucleic acid probes derived from the instant nucleic acid sequences may be used in direct fluorescence in situ hybridization (FISH) mapping (Trask (1991) *Trends Genet.* 7:149–154). Although current methods of FISH mapping favor use of large clones (several to several hundred KB; see Laan et al. (1995) *Genome Res.* 5:13–20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) *J. Lab. Clin. Med.* 11:95–96), polymorphism of PCR-amplified fragments (CAPS; Sheffield et al. (1993) *Genomics* 16:325–332), allele-specific ligation (Landegren et al. (1988) *Science* 241:1077–1080), nucleotide extension reactions (Sokolov (1990) *NucleicAcid Res.* 18:3671), Radiation Hybrid Mapping (Walter et al. (1997) *Nat. Genet.* 7:22–28) and Happy Mapping (Dear and Cook (1989) *Nucleic Acid Res.* 17:6795–6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer (1989) *Proc. Natl. Acad. Sci USA* 86:9402–9406; Koes et al. (1995) *Proc. Natl. Acad. Sci USA* 92:8149–8153; Bensen et al. (1995) *Plant Cell* 7:75–84). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the instant polypeptides. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding the instant polypeptides can be identified and obtained. This mutant plant can then be used to determine or confirm the natural function of the instant polypeptides disclosed herein.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Example 1
Composition of cDNA Libraries; Isolation and Sequencing of cDNA Clones cDNA libraries representing mRNAs from various corn, rice, soybean, and wheat tissues were prepared. The characteristics of the libraries are described below.

TABLE 2 cDNA Libraries from Corn, Rice, Soybean, and Wheat

| Library | Tissue | Clone |
|---|---|---|
| cen3-bs | Corn Endosperm 20 Days After Pollination | cen3-bs.pk0018.a4 |
| cen3n | Corn Endosperm 20 Days After Pollination* | cen3n.pk0129.d6 |
| cr1 | Corn Root From 7 Day Old Seedlings | cr1.pk0029.d11 |
| rr1 | Rice Root of Two Week Old Developing Seedling | rr1.pk0045.b9 |
| rr1 | Rice Root of Two Week Old Developing Seedling | rr1.pk0074.e3 |
| sdc1c | Soybean Developing Cotyledon (3–5 mm) | sdc1c.pk0004.b11 |
| sfl1 | Soybean Immature Flower | sfl1.pk0070.a9 |
| sgc2c | Soybean Cotyledon 12–20 Days After Germination (Mature Green) | sgs2c.pk004.d12 |
| sgc5c | Soybean (Cotyledon 15–24 Days After Germination (¾ yellow) | sgs5c.pk0003.f9 |
| sr1 | Soybean Root | sr1.pk0018.g3 |
| src2c | Soybean 8 Day Old Root Infected With Cyst Nematode | src2c.pk001.o5 |
| wle1n | Wheat Leaf From 7 Day Old Etiolated Seedling* | wle1n.pk0043.b1 |
| wle1n | Wheat Leaf From 7 Day Old Etiolated Seedling* | wle1n.pk0054.a2 |
| wre1n | Wheat Root From 7 Day Old Etiolated Seedling* | wre1n.pk0057.d11 |

*These libraries were normalized essentially as described in U.S. Pat. No. 5,482,845, incorporated herein by reference.

cDNA libraries may be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pbluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) Science 252:1651–1656). The resulting ESTs are analyzed using a Perkin Elmer Model 377 fluorescent sequencer.

Example 2
Identification of cDNA Clones cDNA clones encoding enzymes involved in sterol metabolism were identified by conducting BLAST (Basic Local Alignment Search Tool; Altschul et al. (1993) *J. Mol. Biol.* 215:403–410) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) *Nat. Genet.* 3:266–272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

Example 3
Characterization of cDNA Clones Encoding C-4 Methyl Sterol Oxidase The BLASTX search using the EST sequences from clones listed in Table 3 revealed similarity of the polypeptides encoded by the cDNAs to a predicted open reading frame from *Arabidopsis thaliana*, Neurorep 1 from *Rattus norvegicus* and C-4 methyl sterol oxidase from *Homo sapiens* (NCBI General Identifier Nos. 2827552, 2605606, and 2498340, respectively). Shown in Table 3 are the BLAST results for individual ESTs ("EST"), OR contigs assembled from two or more ESTs ("Contig"):

TABLE 3

BLAST Results for Sequences Encoding Polypeptides Homologous to C-4 Methyl Sterol Oxidase

| | | BLAST pLog Score | | |
|---|---|---|---|---|
| Clone | Status | 2827552 | 2605606 | 2498340 |
| cen3-bs.pk0018.a4 | EST | — | 12.40 | 12.00 |
| rr1.pk0074.e3 | EST | 28.40 | 18.00 | 18.30 |
| Contig of: sgs2c.pk004.d12 sfl1.pk0070.a9 | Contig | | 8.30 | 9.10 |
| Contig of: wre1n.pk0057.d11 wle1n.pk0054.a2 | Contig | 53.70 | 38.52 | 39.10 |

The BLASTP search using the cDNA sequences from clones listed in Table 4 revealed similarity of the polypeptides encoded by the cDNAs to a putative C-4 methyl sterol oxidase from *Arabidopsis thaliana*, Neurorep 1 from *Rattus norvegicus*, and a sterol-C4-methyl oxidase-like from *Homo sapiens* (NCBI General Identifier Nos. 3980396, 2605606, and 5803157, respectively). Shown in Table 4 are the BLAST results for the sequences of the entire cDNA inserts comprising the indicated cDNA clones ("FIS"), or sequences encoding the entire protein derived from an FIS ("CGS"):

TABLE 4

BLAST Results for Sequences Encoding Polypeptides Homologous to C-4 Methyl Sterol Oxidase

| Clone | Status | BLAST pLog Score | | |
|---|---|---|---|---|
| | | 3980396 | 2605606 | 5803157 |
| cen3-bs.pk0018.a4:fis | CGS | 120.00 | 53.15 | 53.05 |
| rr1.pk0074.e3:fis | FIS | 45.70 | 17.00 | 17.10 |
| sgs2c.pk004.d12:fis* | CGS | 130.00 | 51.40 | 50.52 |

*This CGS includes the entire sequence of the soybean contig of Table 3.

The data in Table 5 represents a calculation of the percent identity of the amino acid sequences set forth in SEQ ID NOs:20, 8, 22, and 24 and the *Arabidopsis thaliana*, *Rattus norvegicus*, and *Homo sapiens* sequences (NCBI General Identifier Nos. 3980396, 2605606, and 5803157, respectively).

TABLE 5

Percent Identity of Amino Acid Sequences Deduced From the Nucleotide Sequences of cDNA Clones Encoding Polypeptides Homologous to C-4 Methyl Sterol Oxidase

| | Percent Identity to | | |
|---|---|---|---|
| SEQ ID NO. | 3980396 | 2605606 | 5803157 |
| 20 | 73.9 | 33.0 | 33.3 |
| 8 | 80.4 | 38.1 | 38.1 |
| 22 | 83.4 | 32.2 | 32.2 |
| 24 | 90.7 | 47.2 | 48.1 |

Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of a rice and a wheat, and entire corn and soybean C-4 methyl sterol oxidase. These sequences represent the first corn, rice, soybean, and wheat sequences encoding C-4 methyl sterol oxidase.

Example 4

Characterization of cDNA Clones Encoding Steroid 5-alpha Reductase

The BLASTX search using the EST sequences from clones listed in Table 6 revealed similarity of the polypeptides encoded by the cDNAs to steroid reductase DET2 from *Arabidopsis thaliana* and steroid 5-alpha reductase from *Rattus* sp (NCBI General Identifier Nos. 1280611 and 2507119, respectively). The *Arabidopsis thaliana* protein has been shown to behave as a steroid 5-alpha reductase (Li et al.(1997) *Proc. Natl. Acad. Sci. USA* 94:3554–3559). Shown in Table 6 are the BLAST results for individual ESTs ("EST"):

TABLE 6

BLAST Results for Sequences Encoding Polypeptides Homologous to Steroid 5-alpha Reductase

| Clone | Status | BLAST pLog Score | |
|---|---|---|---|
| | | 1280611 | 2507119 |
| cen3n.pk0129.d6 | EST | 28.70 | 13.52 |
| wle1n.pk0043.b1 | EST | 8.30 | 10.05 |

The BLASTP search using the sequence from the entire insert in clone wle1n.pk0043.b1:fis revealed similarity of the polypeptide encoded by the cDNAs to a putative open reading frame and to the steroid reductase DET2 from *Arabidopsis thaliana* (NCBI General Identifier Nos. 4589974 and 1280611, respectively) with pLog values of 43.52 and 12.00.

The data in Table 7 represents a calculation of the percent identity of the amino acid sequences set forth in SEQ ID NOs:10 and 26 and the *Arabidopsis thaliana* DET2 sequence (NCBI General Identifier No. 1280611).

TABLE 7

Percent Identity of Amino Acid Sequences Deduced From the Nucleotide Sequences of cDNA Clones Encoding Polypeptides Homologous to Steroid 5-alpha Reductase

| SEQ ID NO. | Percent Identity to 1280611 |
|---|---|
| 10 | 61.6 |
| 26 | 26.5 |

Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of a corn and a wheat steroid 5-alpha reductase. These sequences represent the first corn and wheat sequences encoding steroid 5-alpha reductase.

Example 5

Characterization of cDNA Clones Encoding Sterol-C-Methyl Transferase

The BLASTX search using the EST sequences from clones listed in Table 8 revealed similarity of the polypeptides encoded by the cDNAs to S-adenosyl-methionine-sterol-C-methyltransferase from *Nicotiana tabacum* and 24-sterol C-methyltransferase from *Arabidopsis thaliana* (NCBI General Identifier No. 2246454 and 2129517, respectively). Shown in Table 8 are the BLAST results for individual ESTs ("EST"), or contigs assembled from two or more ESTs ("Contig"):

TABLE 8

BLAST Results for Sequences Encoding Polypeptides Homologous to Sterol-C- Methyltransferase

| | | BLAST pLog Score | |
|---|---|---|---|
| Clone | Status | 2246454 | 2129517 |
| cr1.pk0029.d11 | EST | 54.52 | 50.30 |
| rr1.pk0045.b9 | EST | 40.70 | 41.70 |
| Contig of: sgs5c.pk0003.f9 src2c.pk001.o5 sdc1c.pk0004.b11 sr1.k0018.g3 | Contig | 95.40 | 104.00 |

The BLASTP search using the cDNA sequences from clones listed in Table 9 revealed similarity of the polypeptides encoded by the cDNAs to C24(1)methyltransferase from *Oryza sativa*, and S-adenosyl-methionine-sterol-C-methyltransferase from *Nicotiana tabacum* (NCBI General Identifier Nos. 3560533 and 2246454, respectively). Shown in Table 9 are the BLAST results for the sequences of the entire cDNA inserts comprising the indicated cDNA clones ("FIS"), or sequences encoding the entire protein derived from an FIS ("CGS"):

TABLE 9

BLAST Results for Sequences Encoding Polypeptides Homologous to Sterol-C-Methyl Transferase

| Clone | Status | NCBI General Identifier No. | BLAST pLog Score |
|---|---|---|---|
| cr1.pk0029.d11:fis | FIS | 3560533 | 116.0 |
| sr1.pk0018.g3:fis* | CGS | 2246454 | >254.0 |

*This CGS includes the entire sequence of the soybean contig of Table 8.

The data in Table 10 represents a calculation of the percent identity of the amino acid sequences set forth in SEQ ID NOs:28 and 30 and the *Oryza sativa* and *Nicotiana tabacum* sequences (NCBI General Identifier Nos. 3560533 and 2246454, respectively).

TABLE 10

Percent Identity of Amino Acid Sequences Deduced From the Nucleotide Sequences of cDNA Clones Encoding Polypeptides Homologous to Sterol-C-Methyl Transferase

| | Percent Identity to | |
|---|---|---|
| SEQ ID NO. | 3560533 | 2246454 |
| 28 | 87.2 | 68.3 |
| 30 | 69.2 | 85.6 |

Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of a corn and an entire soybean sterol-C-methyl transferase. These sequences represent the first corn and soybean sequences encoding sterol-C-methyl transferase.

Example 6
Expression of Chimeric Genes in Monocot Cells

A chimeric gene comprising a cDNA encoding the instant polypeptides in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML103. Plasmid pML103 has been deposited under the terms of the Budapest Treaty at ATCC (American Type Culture Collection, 10801 University Blvd., Manassas, VA 20110–2209), and bears accession number ATCC 97366. The DNA segment from pML 103 contains a 1.05 kb SalI-NcoI promoter fragment of the maize 27 kD zein gene and a 0.96 kb SmaI-SalI fragment from the 3' end of the maize 10 kD zein gene in the vector pGem9Zf (+) (Promega). Vector and insert DNA can be ligated at 15° C. overnight, essentially as described (Maniatis). The ligated DNA may then be used to transform *E. coli* XL1-Blue (Epicurian Coli XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric gene encoding, in the 5' to 3' direction, the maize 27 kD zein promoter, a cDNA fragment encoding the instant polypeptides, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) *Sci. Sin. Peking* 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810–812) and the 3' region of the nopaline synthase gene from the T-DNA of the Ti plasmid of *Agrobacterium tumefaciens*.

The particle bombardment method (Klein et al. (1987) *Nature* 327:70–73) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) *Bio/Technology* 8:833–839).

Example 7
Expression of Chimeric Genes in Dicot Cells

A seed-specific expression cassette composed of the promoter and transcription terminator from the gene encoding the β subunit of the seed storage protein phaseolin from the bean *Phaseolus vulgaris* (Doyle et al. (1986) *J. Biol. Chem.* 261:9228–9238) can be used for expression of the instant polypeptides in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embryos may then be transformed with the expression vector comprising sequences encoding the instant polypeptides. To induce somatic embryos, cotyledons, 3–5 mm in length dissected from surface sterilized, immature seeds of the soybean cultivar A2872, can be cultured in the light or dark at 26° C. on an appropriate agar medium for 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) *Nature* (London) 327:70–73, U.S. Pat. No. 4,945,050). A DuPont Biolistic™ PDS1000/HE instrument (helium retrofit) can be used for these transformations.

A selectable marker gene which can be used to facilitate soybean transformation is a chimeric gene composed of the 35S promoter from Cauliflower Mosaic Virus (Odell et al. (1985) *Nature* 313:810–812), the hygromycin phosphotransferase gene from plasmid pJR225 (from *E. coli*; Gritz et al.(1983) *Gene* 25:179–188) and the 3' region of the nopaline synthase gene from the T-DNA of the Ti plasmid of *Agrobacterium tumefaciens*. The seed expression cassette comprising the phaseolin 5' region, the fragment encoding the instant polypeptides and the phaseolin 3' region can be isolated as a restriction fragment. This fragment can then be inserted into a unique restriction site of the vector carrying the marker gene.

To 50 μL of a 60 mg/mL 1 μm gold particle suspension is added (in order): 5 μL DNA (1 μg/μL), 20 μl spermidine (0.1 M), and 50 μL CaCl$_2$ (2.5 M). The particle preparation is then agitated for three minutes, spun in a microfuge for 10 seconds and the supernatant removed. The DNA-coated particles are then washed once in 400 μL 70% ethanol and resuspended in 40 μL of anhydrous ethanol. The DNA/particle suspension can be sonicated three times for one second each. Five μL of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 8
Expression of Chimeric Genes in Microbial Cells

The cDNAs encoding the instant polypeptides can be inserted into the T7 E. coli expression vector pBT430. This vector is a derivative of pET-3a (Rosenberg et al. (1987) Gene 56:125–135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% NuSieve GTG™ low melting agarose gel (FMC). Buffer and agarose contain 10 μg/ml ethidium bromide for visualization of the DNA fragment. The fragment can then be purified from the agarose gel by digestion with GELase™ (Epicentre Technologies) according to the manufacturer's instructions, ethanol precipitated, dried and resuspended in 20 μL of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 μg/mL ampicillin. Transformants containing the gene encoding the instant polypeptides are then screened for the correct orientation with respect to the T7 promoter by restriction enzyme analysis.

For high level expression, a plasmid clone with the cDNA insert in the correct orientation relative to the T7 promoter can be transformed into E. coli strain BL21(DE3) (Studier et al. (1986) J. Mol. Biol. 189:113–130). Cultures are grown in LB medium containing ampicillin (100 mg/L) at 25° C. At an optical density at 600 nm of approximately 1, IPTG (isopropylthio-β-galactoside, the inducer) can be added to a fmal concentration of 0.4 mM and incubation can be continued for 3 h at 25°. Cells are then harvested by centrifugation and re-suspended in 50 μL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One μg of protein from the soluble fraction of the culture can be separated by SDS-polyacrylamide gel electrophoresis. Gels can be observed for protein bands migrating at the expected molecular weight.

Example 9
Evaluating Compounds for Their Ability to Inhibit the Activity of Enzymes Involved in Sterol Metabolism The polypeptides described herein may be produced using any number of methods known to those skilled in the art. Such methods include, but are not limited to, expression in bacteria as described in Example 8, or expression in eukaryotic cell culture, in planta, and using viral expression systems in suitably infected organisms or cell lines. The instant polypeptides may be expressed either as mature forms of the proteins as observed in vivo or as fusion proteins by covalent attachment to a variety of enzymes, proteins or affinity tags. Common fusion protein partners include glutathione S-transferase ("GST"), thioredoxin ("Trx"), maltose binding protein, and C- and/or N-terminal hexahistidine polypeptide ("(His)$_6$"). The fusion proteins may be engineered with a protease recognition site at the fusion point so that fusion partners can be separated by protease digestion to yield intact mature enzyme. Examples of such proteases include thrombin, enterokinase and factor Xa. However, any protease can be used which specifically cleaves the peptide connecting the fusion protein and the enzyme.

Purification of the instant polypeptides, if desired, may utilize any number of separation technologies familiar to those skilled in the art of protein purification. Examples of such methods include, but are not limited to, homogenization, filtration, centrifugation, heat denaturation, ammonium sulfate precipitation, desalting, pH precipitation, ion exchange chromatography, hydrophobic interaction chromatography and affinity chromatography, wherein the affinity ligand represents a substrate, substrate analog or inhibitor. When the instant polypeptides are expressed as fusion proteins, the purification protocol may include the use of an affinity resin which is specific for the fusion protein tag attached to the expressed enzyme or an affinity resin containing ligands which are specific for the enzyme. For example, the instant polypeptides may be expressed as a fusion protein coupled to the C-terminus of thioredoxin. In addition, a (His)$_6$ peptide may be engineered into the N-terminus of the fused thioredoxin moiety to afford additional opportunities for affinity purification. Other suitable affinity resins could be synthesized by linking the appropriate ligands to any suitable resin such as Sepharose-4B. In an alternate embodiment, a thioredoxin fusion protein may be eluted using dithiothreitol; however, elution may be accomplished using other reagents which interact to displace the thioredoxin from the resin. These reagents include β-mercaptoethanol or other reduced thiol. The eluted fusion protein may be subjected to further purification by traditional means as stated above, if desired. Proteolytic cleavage of the thioredoxin fusion protein and the enzyme may be accomplished after the fusion protein is purified or while the protein is still bound to the ThioBond™ affinity resin or other resin.

Crude, partially purified or purified enzyme, either alone or as a fusion protein, may be utilized in assays for the evaluation of compounds for their ability to inhibit enzymatic activation of the instant polypeptides disclosed herein. Assays may be conducted under well known experimental conditions which permit optimal enzymatic activity. For example, assays for sterol 5alpha reductase are presented by Fujioka et al. (1997) Plant Cell 9:1951–1962. Assays for sterol-C-methyltransferase are presented by Schaller et al. (1998) Plant Phys. 118:461–469. Assays for steroid 5alpha-reductase are presented by Houston et al. (1985) J. Steroid. Biochem. 22:461–467.

What is claimed is:

1. An isolated polynucleotide comprising:
   (a) a nucleotide sequence encoding a polypeptide having C-4 Methyl Sterol Oxidase activity, wherein the amino acid sequence of the polypeptide and the amino acid sequence of SEQ ID NO:20 have at least 95% sequence identity based on the Clustal alignment method; or
   (b) the complement of the nucleotide sequence, wherein the complement and the nucleotide sequence contain the same number of nucleotides and are 100% complementary.

2. The polynucleotide of claim 1 wherein the polypeptide comprises the amino acid sequence of SEQ ID NO:20.

3. The polynucleotide of claim 1, wherein the nucleotide sequence comprises the nucleotide sequence of SEQ ID NO:19.

4. A recombinant DNA construct comprising the polynucleotide of claim 1 operably linked to at least one regulatory sequence.

5. A cell comprising the polynucleotide of claim 1.

6. The cell of claim 5, wherein the cell is selected from the group consisting of a yeast cell, a bacterial cell and a plant cell.

7. A virus comprising the polynucleotide of claim 1.

8. A transgenic plant comprising the polynucleotide of claim 1.

9. A method for transforming a cell comprising introducing into a cell the polynucleotide of claim 1.

10. A method for producing a transgenic plant comprising (a) transforming a plant cell with the polynucleotide of claim 1, and (b) regenerating a transgenic plant from the transformed plant cell.

11. A vector comprising the polynucleotide of claim 1.

12. A seed comprising the polynucleotide of claim 1.

* * * * *